US010160789B2

(12) United States Patent
Matoba et al.

(10) Patent No.: US 10,160,789 B2
(45) Date of Patent: Dec. 25, 2018

(54) POLYPEPTIDES HAVING IMMUNOACTIVATING ACTIVITY AND METHODS OF PRODUCING THE SAME

(75) Inventors: Nobuyuki Matoba, Owensboro, KY (US); Krystal Hamorsky, Owensboro, KY (US)

(73) Assignee: University of Louisville Research Foundation, Inc., Louisville, KY (US)

( * ) Notice: Subject to any disclaimer, the term of this patent is extended or adjusted under 35 U.S.C. 154(b) by 1083 days.

(21) Appl. No.: 14/005,388

(22) PCT Filed: Mar. 14, 2012

(86) PCT No.: PCT/US2012/029072

§ 371 (c)(1), (2), (4) Date: Oct. 9, 2013

(87) PCT Pub. No.: WO2012/125720

PCT Pub. Date: Sep. 20, 2012

(65) Prior Publication Data

US 2014/0286986 A1 Sep. 25, 2014

Related U.S. Application Data

(60) Provisional application No. 61/452,308, filed on Mar. 14, 2011.

(51) Int. Cl.

| | |
|---|---|
| ***C07K 14/28*** | (2006.01) |
| ***A61K 39/106*** | (2006.01) |
| ***C12N 15/82*** | (2006.01) |
| ***A61K 39/02*** | (2006.01) |
| *A61K 38/00* | (2006.01) |
| *A61K 39/00* | (2006.01) |

(52) U.S. Cl.

CPC ............ *C07K 14/28* (2013.01); *A61K 39/107* (2013.01); *C12N 15/8258* (2013.01); *A61K 38/00* (2013.01); *A61K 2039/542* (2013.01); *C07K 2319/02* (2013.01); *C07K 2319/04* (2013.01); *Y02A 50/472* (2018.01)

(58) Field of Classification Search

None

See application file for complete search history.

(56) References Cited

U.S. PATENT DOCUMENTS

| | | | | |
|---|---|---|---|---|
| 6,395,964 | B1 | 5/2002 | Arntzen et al. | |
| 6,777,546 | B2 | 8/2004 | Langridge et al. | |
| 7,556,806 | B2 | 7/2009 | Wang | |
| 2002/0055618 | A1 | 5/2002 | Langridge et al. | |
| 2003/0021803 | A1 | 1/2003 | Langridge et al. | |
| 2003/0165543 | A1 | 9/2003 | Langridge et al. | |
| 2003/0191076 | A1 | 10/2003 | Wesselingh et al. | |
| 2005/0044588 | A1 | 2/2005 | Langridge et al. | |
| 2005/0186219 | A1 | 8/2005 | Langridge et al. | |
| 2005/0241024 | A1 | 10/2005 | Langridge et al. | |
| 2005/0244424 | A1 | 11/2005 | Wang | |
| 2005/0277635 | A1 | 12/2005 | Bornemann et al. | |
| 2006/0199778 | A1 | 9/2006 | Ellis-Behnke et al. | |
| 2006/0211087 | A1* | 9/2006 | Roosild .................. | C07K 14/32 435/69.1 |
| 2006/0286096 | A1 | 12/2006 | Swain et al. | |
| 2007/0192905 | A1 | 8/2007 | Piller et al. | |
| 2008/0060092 | A1* | 3/2008 | Dickey .................. | C07K 14/47 800/276 |
| 2008/0233083 | A1* | 9/2008 | Ansari ................... | A61K 39/12 424/85.2 |
| 2008/0279877 | A1* | 11/2008 | Yusibov ................ | A61K 39/12 424/186.1 |
| 2009/0081256 | A1 | 3/2009 | Langridge et al. | |
| 2009/0155297 | A1 | 6/2009 | Mrsny | |
| 2009/0214570 | A1 | 8/2009 | Mrsny et al. | |
| 2012/0100171 | A1 | 4/2012 | Henry | |
| 2012/0100609 | A1 | 4/2012 | Crawford et al. | |

OTHER PUBLICATIONS

Kang et al (Molecular Breeding, 2004, 13:143-153).*
Mishra et al (Journal of Biotechnology, 2006, 127(1): 95-108).*
GenBank Accession No. AAD51360.1 (published Nov 1999).*
Lebens et al (Infection and Immunity, 1996, 64(6): 2144-2150).*
GenBank Accession No. CAA00098.1 (published Dec. 2005; appended to office action).*
Balzarini J. (2007). "Targeting the glycans of glycoproteins: a novel paradigm for antiviral therapy." Nat Rev Microbiol. 5(8):583-97.
Fields J, et al. (1960) "Synthetic polyelectrolytes as tumour inhibitors." Nature 186:778-780.
Gleba Y, et al. (2005). "Magnifection—a new platform for expressing recombinant vaccines in plants." Vaccine. 23(17-18):2042-8.
Keler T, et al. (2004). "Mannose receptor-targeted vaccines." Expert opinion on biological therapy. 4(12):1953-62.
Klinman et al., (1996). "Cpg motifs present in bacterial DNA rapidly induce lymphocytes to secrete interleukin 6, interleukin 12, and interferon •." Proc. Natl. Acad. Sci., USA, 93:2879-2883. WO98/16247.

(Continued)

*Primary Examiner* — Stephen Uyeno

(74) *Attorney, Agent, or Firm* — Hamilton, Brook, Smith & Reynolds, P.C.

(57) ABSTRACT

Isolated polypeptides are provided that comprise a cholera toxin B subunit variant having one or more modifications to increase the expression of the polypeptide in a plant cell. Nucleic acids sequences, vectors, and plant cells for expressing the cholera toxin B subunit variant polypeptides are also provided. Further provided are methods for producing the cholera toxin B subunit variant polypeptides that include the steps of transforming a plant cell with a nucleic acid encoding the cholera toxin B subunit variant polypeptides; expressing the variant polypeptides; and purifying the polypeptides. Still further provided are methods of isolating the variant polypeptides that include the steps of obtaining a plant cell expressing the cholera toxin B subunit variant polypeptides; extracting the cholera toxin B subunit variant polypeptides from the plant cell; and purifying the cholera toxin B subunit variant polypeptides. Methods of eliciting an immune response are also provided.

6 Claims, 9 Drawing Sheets

Specification includes a Sequence Listing.

(56) References Cited

OTHER PUBLICATIONS

Marillonnet S, et al. (2004). "In planta engineering of viral RNA replicons: efficient assembly by recombination of DNA modules delivered by Agrobacterium." Proc Natl Acad Sci USA. 101(18):6852-7.
Matoba N, et al. (2004). "A mucosally targeted subunit vaccine candidate eliciting HIV-1 transcytosis-blocking Abs." Proc Natl Acad Sci USA. 101(37):3584-9.
Matoba N, et al. (2006). ."Humoral immune responses by prime-boost heterologous route immunizations with CTB-MPR(649-684), a mucosal subunit HIV/AIDS vaccine candidate." Vaccine. 24(23):5047-55.
Matoba N, et al. (2008). "Transcytosis-blocking Abs elicited by an oligomeric immunogen based on the membrane proximal region of HIV-1 gp41 target non-neutralizing epitopes." Curr HIV Res. 6(3):218-29.
Matoba N, et al. (2009). "Biochemical and immunological characterization of the plant-derived candidate human immunodeficiency virus type 1 mucosal vaccine CTB-MPR(649-684)." Plant Biotechnol J. 7(2):129-45.
Matoba N, et al. (2011). "Recombinant Protein Expression in Nicotiana." Methods Mol Biol. 701:199-219.
Hong, Li , et al. (1996). "Immunocytochemical Characterization of CD44 Molecules Expressed in Human Brain Metastases." Pharmeuropa. vol. 8, No. 2.
Powell M, et al. (1995). of "Vaccine Design, The Subunit and Adjuvant Approach" published by Plenum Press p. 147 and the emulsion MF59 described on p. 183 of the same work.
Sheng KC, et al. (2008). "Delivery of antigen using a novel mannosylated dendrimer potentiates immunogenicity in vitro and in vivo." Eur J Immunol. 38(2):424-36.
ISA/KR, International Preliminary Report on Patentability and Written Opinion issued in related international application No. PCT/US2012/029072, dated Sep. 17, 2013.
ISA/KR, International Search Report issued in related international application No. PCT/US2012/029072, dated Sep. 24, 2012.
Arakawa, et al. (1997). "Expression of cholera toxin B subunit oligomers in transgenic potato plants," Transgenic Research, vol. 6, pp. 403-413.
NCBI, GenBank accession No. CAA00066.1 (Dec. 1, 2005).
Mikschofsky, et al. (2009). "Cholera toxin B (CTB) is functional as an adjuvant for cytoplasmic proteins if directed to the endoplasmic reticulum (ER), but not to the cytoplasm of plants," Plant Science, vol. 177, pp. 35-42.

* cited by examiner

| | $IC_{50}$ (nM) |
|---|---|
| 1. Native CTB | 8.97 |
| 2. Plant CTB, aglyc. | 5.65 |
| 3. Plant CTB, glyc. | 11.52 |

POLYPEPTIDES HAVING IMMUNOACTIVATING ACTIVITY AND METHODS OF PRODUCING THE SAME

RELATED APPLICATIONS

This application claims priority from U.S. Provisional Application Ser. No. 61/452,308, filed Mar. 14, 2011, the entire disclosure of which is incorporated herein by this reference.

GOVERNMENT INTEREST

This invention was made with government support under Grant No. W81XWH-10-2-0082 awarded by the United States Department of Defense. The government has certain rights in the invention.

TECHNICAL FIELD

The presently-disclosed subject matter relates to polypeptides having immunoactivating activity and methods of producing the same. In particular, the presently-disclosed subject matter relates to immunoactivating polypeptides comprising a cholera toxin B subunit variant having one or more modifications to increase the expression of the variant in the plant cell, as well as methods of producing those polypeptides in a plant cell.

BACKGROUND

Cholera is a serious diarrheal disease caused by the pathogenic strains of *Vibrio cholerae*, which leads to severe dehydration and even death within 18 hours if left untreated. Indeed, the World Health Organization (WHO) has estimated that 3 to 5 million cases of cholera occur each year with approximately 100,000 to 130,000 of those cases ending in death.

Despite the severity of cholera, cholera is generally no longer a concern in developed countries. However, it is still a major threat in many developing countries, where a safe water supply and advanced sanitation systems are generally not available. In fact, large outbreaks of cholera sporadically occur every year, as recently seen in Papua New Guinea (2009-2010), Zimbabwe and other African countries (2008-2010), as well as, most recently, in Haiti (2010-present).

Due to recurring outbreaks, implementation of a mass vaccination program for cholera has now been proposed as part of global cholera prevention strategies. Dukoral (Crucell, Netherlands) is an internationally licensed, World Health Organization-prequalified oral cholera vaccine, which contains killed *Vibrio cholerae* bacteria and a recombinant cholera toxin B subunit polypeptide (rCTB; SEQ ID NO: 2) produced in genetically-modified bacterium. This vaccine has been shown to provide protection in greater than 80% of subjects to which it is administered, which is higher than killed *V. cholerae* alone. Nevertheless, production of sufficient doses of the vaccine for mass vaccination campaigns has proven to be challenging, particularly for the rCTB, whose production is significantly hindered by the limited scalability of fermentation-based production.

SUMMARY

The presently-disclosed subject matter meets some or all of the above-identified needs, as will become evident to those of ordinary skill in the art after a study of information provided in this document.

This Summary describes several embodiments of the presently-disclosed subject matter, and in many cases lists variations and permutations of these embodiments. This Summary is merely exemplary of the numerous and varied embodiments. Mention of one or more representative features of a given embodiment is likewise exemplary. Such an embodiment can typically exist with or without the feature(s) mentioned; likewise, those features can be applied to other embodiments of the presently-disclosed subject matter, whether listed in this Summary or not. To avoid excessive repetition, this Summary does not list or suggest all possible combinations of such features.

The presently-disclosed subject matter relates to polypeptides having broad immunoactivating activity and methods of producing the same. In particular, the presently-disclosed subject matter relates to polypeptides comprising a cholera toxin B subunit variant having one or more modifications to increase the expression of the polypeptide in the plant cell, as well as methods of producing those polypeptides in a plant cell.

In some embodiments of the presently-disclosed subject matter, an isolated polypeptide is provided that comprises a cholera toxin B subunit variant having one or more modifications to increase the expression of the polypeptide in a plant cell. In some embodiments, the cholera toxin B subunit variant comprises the sequence of SEQ ID NO: 4, SEQ ID NO: 6, or SEQ ID NO: 25.

In some embodiments of the presently-disclosed polypeptides, the one or more modifications to the cholera toxin B subunit variant polypeptide comprise the addition of a secretory signal peptide selected from the group consisting of a rice alpha-amylase secretory signal peptide, a *Nicotiana plumbaginifolia* calreticulin secretory signal peptide, an apple pectinase secretory signal peptide, and a barley alpha-amylase secretory signal peptide. In some embodiments, the one or more modifications comprise a secretory signal peptide having an amino acid sequence selected from the group consisting of SEQ ID NOS: 18, 20, 22, and 24. In some embodiments, the secretory signal polypeptide is a rice-alpha-amylase secretory signal peptide. In some embodiments, the cholera toxin B subunit variant polypeptide comprises an amino acid sequence selected from the group consisting of SEQ ID NOS: 26-29.

With further regard to the polypeptides of the presently-disclosed subject matter, in some embodiments, the one or more modifications made to the cholera toxin B subunit variant polypeptides comprise the addition of an endoplasmic reticulum retention signal having, in some embodiments, the amino acid sequence KDEL (SEQ ID NO: 31). In some embodiments, the cholera toxin B subunit variant polypeptide comprises two or more N-linked glycosylation sequons, such as, in some embodiments, the polypeptides of SEQ ID NO: 8SEQ ID NO: 10, SEQ ID NO: 12, or SEQ ID NO: 14.

Further provided, in some embodiments of the presently-disclosed subject matter, are pharmaceutical compositions. In some embodiments, a pharmaceutical composition is provided that comprises a polypeptide of the presently-disclosed subject matter and a pharmaceutically-acceptable vehicle, carrier, or excipient. In some embodiments, the pharmaceutical composition further comprises an adjuvant.

Still further provided by the presently-disclosed subject matter are isolated nucleic acid molecules. In some embodiments, an isolated nucleic acid molecule is provided that comprises a nucleic acid sequence encoding a polypeptide of the presently-disclosed subject matter. In some embodiments, the nucleic acids are incorporated into an appropriate expression vector for expressing the polypeptides of the presently-disclosed subject matter in a desired cell, such as, in some embodiments, a plant cell transfected with the vectors, or a progeny of the plant cell, where the cell or the progeny of the cell expresses the polypeptide. In some embodiments, the nucleic acids incorporated into the vectors are operably linked to an expression cassette.

In yet further embodiments of the presently-disclosed subject matter are methods for producing a cholera toxin B subunit variant polypeptide, such as those described herein. In some embodiments, a method of producing a cholera toxin B subunit variant polypeptide is provided that includes the steps of: transforming a plant cell with a nucleic acid encoding a cholera toxin B subunit variant polypeptide having one or more modifications to increase the expression of the variant polypeptide in a plant cell; expressing the cholera toxin B subunit variant polypeptide in the plant cell; and purifying the cholera toxin B subunit variant polypeptide. In some embodiments, the plant cell comprises a *Nicotiana* plant cell, such as, in some embodiments, a *Nicotiana benthamiana* plant cell. In some embodiments, the nucleic acid encoding the cholera toxin B subunit variant polypeptide expressed by the plant cell comprises the sequence of SEQ ID NO: 3, SEQ ID NO: 5, SEQ ID NO: 7, SEQ ID NO: 9, SEQ ID NO: 11, or SEQ ID NO: 13.

In still further embodiments of the presently-disclosed subject matter are methods for isolating a cholera toxin B subunit variant polypeptide from a plant tissue. In some embodiments, an isolation method is provided that comprises: obtaining a plant cell expressing a cholera toxin B subunit variant polypeptide having one or more modifications to increase the expression of the polypeptide in the plant cell; extracting the cholera toxin B subunit variant polypeptide from the plant cell; and purifying the cholera toxin B subunit variant polypeptide from the plant cell. In some embodiments, the step of extracting the cholera toxin B subunit variant polypeptide from the plant cell comprises homogenizing the plant tissue in an aqueous buffer having an acidic pH. In some embodiments, the pH of the aqueous buffer is about 5. In some embodiments, the step of purifying the cholera toxin B subunit variant polypeptide from the plant cell comprises purifying the variant polypeptide using chromatography.

Additionally provided, in some embodiments of the presently-disclosed subject matter, are methods for eliciting an immune response. In some embodiments, a method for eliciting an immune response in a subject is provided that comprises administering to a subject in need thereof an effective amount of a cholera toxin B subunit variant polypeptide of the presently-disclosed subject matter. In some embodiments, administering an effective amount of the cholera toxin B subunit variant polypeptide increases an amount of IgG, IgA, IgM, effector T cells, regulatory T cells, or combinations thereof in a subject. In some embodiments, administering an effective amount of the cholera toxin B subunit variant polypeptide comprises orally administering the cholera toxin B subunit variant polypeptide.

Further advantages of the presently-disclosed subject matter will become evident to those of ordinary skill in the art after a study of the description, Figures, and non-limiting Examples in this document.

BRIEF DESCRIPTION OF THE SEQUENCE LISTING

Figure 1A:
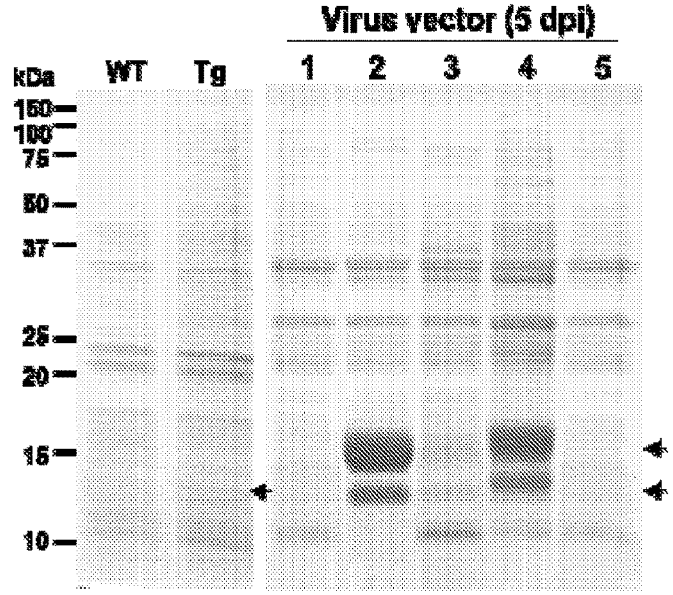
FIGS. 1A and 1B are an image and a graph showing the expression of various cholera toxin B subunit variant polypeptides in *N. benthamiana*, including an image of a SDS-PAGE analysis of leaf extracts containing the various cholera toxin B subunit variant polypeptides (FIG. 1A); and a graph showing the amounts of the various cholera toxin B subunit variant polypeptides present in the leaf extracts based on a GM1-ELISA (FIG. 1B)

SEQ ID NO: 1 is nucleic acid sequence of a wild-type cholera toxin B subunit from *Vibrio cholerae;*

SEQ ID NO: 2 is an amino acid sequence of a wild-type cholera toxin B subunit from *Vibrio cholerae;*

SEQ ID NO: 3 is nucleic acid sequence encoding a cholera toxin B subunit variant polypeptide modified to include a C-terminal endoplasmic reticulum signal and to include no N-linked glycosylation sequons at Asn4;

SEQ ID NO: 4 is an amino acid sequence of a cholera toxin B subunit variant polypeptide modified to include a C-terminal endoplasmic reticulum signal and to include no N-linked glycosylation sequons at Asn4;

SEQ ID NO: 5 is a nucleic acid sequence encoding a cholera toxin B subunit variant polypeptide modified to include a C-terminal endoplasmic reticulum retention signal and having one N-linked glycosylation sequon at Asn4;

SEQ ID NO: 6 is an amino acid sequence of a cholera toxin B subunit variant polypeptide modified to include a C-terminal endoplasmic reticulum retention signal and having one N-linked glycosylation sequon at Asn4;

SEQ ID NO: 7 is a nucleic acid sequence encoding a cholera toxin B subunit variant polypeptide modified to include a C-terminal endoplasmic reticulum retention signal and to include two N-linked glycosylation sequons at Asn4 and Asn103;

SEQ ID NO: 8 is an amino acid sequence of a cholera toxin B subunit variant polypeptide modified to include a C-terminal endoplasmic reticulum retention signal and to include two N-linked glycosylation sequons at Asn4 and Asn103;

SEQ ID NO: 9 is a nucleic acid sequence encoding another cholera toxin B subunit variant polypeptide modified to include a C-terminal endoplasmic reticulum retention signal and to include two N-linked glycosylation sequons at Asn4 and Asn21;

SEQ ID NO: 10 is an amino acid sequence of another cholera toxin B subunit variant polypeptide modified to include a C-terminal endoplasmic reticulum retention signal and to include two N-linked glycosylation sequons at Asn4 and Asn21;

SEQ ID NO: 11 is a nucleic acid sequence encoding a cholera toxin B subunit variant polypeptide modified to include a C-terminal endoplasmic reticulum retention signal and to include three N-linked glycosylation sequons at Asn4, Asn21, and Asn103;

SEQ ID NO: 12 is an amino acid sequence of a cholera toxin B subunit variant polypeptide modified to include a C-terminal endoplasmic reticulum retention signal and to include three N-linked glycosylation sequons at Asn4, Asn21, and Asn103;

SEQ ID NO: 13 is a nucleic acid sequence encoding another cholera toxin B subunit variant polypeptide modified to include a C-terminal endoplasmic reticulum retention signal and to include three N-linked glycosylation sequons at Asn4, Asn21, and Asn103;

SEQ ID NO: 14 is an amino acid sequence of another cholera toxin B subunit variant polypeptide modified to include a C-terminal endoplasmic reticulum retention signal and to include three N-linked glycosylation sequons at Asn4, Asn21, and Asn103;

SEQ ID NO: 15 is a nucleic acid sequence encoding a cholera toxin B subunit variant polypeptide with an N-terminal secretory signal from *Vibrio cholerae* and a C-terminal endoplasmic reticulum retention signal;

SEQ ID NO: 16 is an amino acid sequence of a cholera toxin B subunit variant polypeptide including an N-terminal secretory signal from *Vibrio cholerae* and a C-terminal endoplasmic reticulum retention signal;

SEQ ID NO: 17 is a nucleic acid sequence encoding a rice alpha-amylase secretory signal peptide;

SEQ ID NO: 18 is an amino acid sequence of a rice alpha-amylase secretory signal peptide;

SEQ ID NO: 19 is nucleic acid sequence encoding a *Nicotiana plumbagenifolia* calreticulin secretory signal peptide;

SEQ ID NO: 20 is an amino acid sequence of a *Nicotiana plumbagenifolia* calreticulin secretory signal peptide;

SEQ ID NO: 21 is a nucleic acid sequence encoding an apple pectinase secretory signal peptide;

SEQ ID NO: 22 is an amino acid sequence of an apple pectinase secretory signal peptide;

SEQ ID NO: 23 is a nucleic acid sequence encoding a barley alpha-amylase secretory signal peptide;

SEQ ID NO: 24 is an amino acid sequence encoding a barley alpha-amylase secretory signal peptide;

SEQ ID NO: 25 is an amino acid sequence of a cholera toxin B subunit variant polypeptide including a Ser26→Cys and an Ala102→Cys mutation;

SEQ ID NO: 26 is an amino acid sequence of a cholera toxin B subunit variant polypeptide including a rice alpha-amylase N-terminal secretory signal peptide and a C-terminal endoplasmic reticulum retention signal peptide;

SEQ ID NO: 27 is an amino acid sequence of a cholera toxin B subunit variant polypeptide including a *Nicotiana plumbagenifolia* calreticulin N-terminal secretory signal peptide and a C-terminal endoplasmic reticulum retention signal peptide;

SEQ ID NO: 28 is an amino acid sequence of a cholera toxin B subunit variant polypeptide including an apple pectinase N-terminal secretory signal peptide and a C-terminal endoplasmic reticulum retention signal peptide;

SEQ ID NO: 29 is an amino acid sequence of a cholera toxin B subunit variant polypeptide including a barley alpha-amylase N-terminal secretory signal peptide and a C-terminal endoplasmic reticulum retention signal peptide;

SEQ ID NO: 30 is an amino acid sequence of an exemplary endoplasmic reticulum retention signal peptide, KDEL (SEQ ID NO: 31), including a two amino acid linker, SE, preceding the KDEL sequence (SEQ ID NO: 31); and SEQ ID NO: 31 is an amino acid of the exemplary endoplasmic reticulum retention signal peptide, KDEL.

DESCRIPTION OF EXEMPLARY EMBODIMENTS

The details of one or more embodiments of the presently-disclosed subject matter are set forth in this document. Modifications to embodiments described in this document, and other embodiments, will be evident to those of ordinary skill in the art after a study of the information provided in this document. The information provided in this document, and particularly the specific details of the described exemplary embodiments, is provided primarily for clearness of understanding and no unnecessary limitations are to be understood therefrom. In case of conflict, the specification of this document, including definitions, will control.

Some of the polynucleotide and polypeptide sequences disclosed herein are cross-referenced to GENBANK®/GENPEPT® accession numbers. The sequences cross-referenced in the GENBANK®/GENPEPT® database are expressly incorporated by reference as are equivalent and related sequences present in GENBANK®/GENPEPT® or other public databases. Also expressly incorporated herein by reference are all annotations present in the GENBANK®/GENPEPT® database associated with the sequences disclosed herein. Unless otherwise indicated or apparent, the references to the GENBANK®/GENPEPT® database are references to the most recent version of the database as of the filing date of this Application.

While the following terms are believed to be well understood by one of ordinary skill in the art, definitions are set forth to facilitate explanation of the presently-disclosed subject matter. Unless defined otherwise, all technical and scientific terms used herein have the same meaning as commonly understood by one of ordinary skill in the art to which the presently-disclosed subject matter belongs. Although any methods, devices, and materials similar or equivalent to those described herein can be used in the practice or testing of the presently-disclosed subject matter, representative methods, devices, and materials are now described.

Following long-standing patent law convention, the terms "a," "an," and "the" refer to "one or more" when used in this application, including the claims. Thus, for example, reference to "a cell" includes a plurality of such cells, and so forth.

Unless otherwise indicated, all numbers expressing quantities of ingredients, properties such as reaction conditions, and so forth used in the specification and claims are to be understood as being modified in all instances by the term "about." Accordingly, unless indicated to the contrary, the numerical parameters set forth in this specification and claims are approximations that can vary depending upon the desired properties sought to be obtained by the presently-disclosed subject matter.

As used herein, the term "about," when referring to a value or to an amount of mass, weight, time, volume, concentration or percentage is meant to encompass variations of in some embodiments ±20%, in some embodiments ±10%, in some embodiments ±5%, in some embodiments ±1%, in some embodiments ±0.5%, and in some embodiments ±0.1% from the specified amount, as such variations are appropriate to perform the disclosed method.

As used herein, ranges can be expressed as from "about" one particular value, and/or to "about" another particular value. It is also understood that there are a number of values disclosed herein, and that each value is also herein disclosed as "about" that particular value in addition to the value itself. For example, if the value "10" is disclosed, then "about 10" is also disclosed. It is also understood that each unit between two particular units are also disclosed. For example, if 10 and 15 are disclosed, then 11, 12, 13, and 14 are also disclosed.

Glycans are polysaccharides or oligosaccharides that are commonly attached to proteins in the endoplasmic reticulum of cells. This attachment occurs via the nitrogen atom in the side chain of the asparagine residue (i.e., amino acid) of the three amino acid sequence Asn-X-Ser or Asn-X-Thr, which are also referred to as N-linked glycosylation sequons, where X can be any amino acid except proline. In other words, the presence of the N-linked glycosylation sequon in proteins leads to the formation of glycoproteins and proteoglycans, which are, generally, found on the exterior surface of eukaryotic cells and, to a certain degree, in prokaryotes.

Glycans are also widely found on the surface of the enveloped viruses that constitute a large group of viral pathogens. Mannose (Man) represents a major fraction of these envelope carbohydrates, often comprising a cluster of N-linked high (H)-Man-type glycans. In this regard, and because such a structure is not commonly found in host glycoproteins, targeting the sugar cluster of N-linked high (H)-Man-type glycans on the envelop of viruses is believed to be a strategy to block the transmission and infection of enveloped viruses, including a number of human immunodeficiency virus (HIV) strains, as well as hepatitis C, influenza, Ebola, and Marburg viruses that have been shown to be neutralized by Man-specific lectins. Despite this possible strategy, however, due to the poor antigenicity and immunogenicity of sugar molecules, induction of carbohydrate-specific antibodies has generally been a major challenge in modern vaccinology.

To that end, the presently-disclosed subject matter is based, at least in part, on the discovery of polypeptides that are capable of inducing H-Man-specific antiviral antibodies by: presenting multiple H-Man glycans in a dense cluster as found on viruses; conjugating H-Man glycans with a highly immunogenic protein; and/or inducing high-avidity immunoglobulins (Igs) that can tightly bind to flexible carbohydrate epitopes through multiple antigen-binding sites. In particular, it has been determined that variant polypeptides derived from an enteric bacterial cholera toxin B subunit can be produced and used to display multiple N-linked H-Man glycans that mimic a virus-like carbohydrate cluster, such that, upon immunization of a subject, the immunogen efficiently induces secretory IgA and IgG along with other mucosal and systemic antibodies to provide a mechanism of protection against the transmission and infection of enveloped viruses. Furthermore, it has been determined that H-Man glycan-displaying cholera toxin B subunit variant polypeptides can be developed as a vaccine scaffold to carry various antigens and efficiently stimulate mucosal and systemic immune systems. It has also been determined that the N-glycosylated cholera toxin B subunit variant polypeptides can exhibit higher vaccine efficacy against cholera. Additionally, it has been discovered that these variant polypeptides can be configured to be effectively produced in a plant-based platform, thus making these immunogens capable of being produced in an economical manner and on a large-scale.

The presently-disclosed subject matter includes polypeptides having broad immunoactivating activity, including the induction of H-Man glycan-specific antibodies, as well as methods for producing and purifying such polypeptides. In some embodiments of the presently-disclosed subject matter, isolated variant polypeptides are provided. In some embodiments, an isolated variant polypeptide is provided that comprises a cholera toxin B subunit variant having one or more modifications to increase the expression of the variant polypeptide in a plant cell.

As would be recognized by those of ordinary skill in the art, cholera toxin is an oligomeric protein complex, which is secreted by the bacterium *Vibrio cholerae* and is thought to be responsible for the enteric symptoms characteristic of a cholera infection. The cholera toxin itself is generally composed of six protein subunits, namely a single copy of the A subunit, which is thought to be the toxic portion of the molecule responsible for its enzymatic action; and five copies of the B subunit, which form a pentameric ring and are thought to comprise the non-toxic portions of the molecule responsible for binding to receptors, such as the GM1 ganglioside receptor, which contains a glycosphingolipid (e.g., a ceramide and oligosaccharide) with one sialic acid and which is attached to the surface of a host cell. As such, the term "cholera toxin B subunit" is used herein to refer to a single B subunit of the cholera toxin as well as to B subunits of the cholera toxic in the form of multimers (e.g., in a pentameric form). Exemplary nucleic acid and amino acid sequence of a native cholera toxin B subunit polypeptide from wild-type *Vibrio cholerae* are provided herein in SEQ ID NOS: 1 and 2.

The terms "polypeptide," "protein," and "peptide," which are used interchangeably herein, refer to a polymer of the 20 protein amino acids, or amino acid analogs, regardless of its size or function. Although "protein" is often used in reference to relatively large polypeptides, and "peptide" is often used in reference to small polypeptides, usage of these terms in the art overlaps and varies. The term "polypeptide" as used herein refers to peptides, polypeptides, and proteins, unless otherwise noted. The terms "protein," "polypeptide," and "peptide" are used interchangeably herein when referring to a gene product. Thus, exemplary polypeptides include gene products, naturally occurring or native proteins, homologs, orthologs, paralogs, fragments and other equivalents, variants, and analogs of the foregoing. The term "native," when used with reference to a polypeptide, refers to a polypeptide that is encoded by a gene that is naturally present in the genome of an untransformed cell.

The terms "polypeptide fragment" or "fragment," when used in reference to a reference polypeptide, refers to a polypeptide in which amino acid residues are deleted as compared to the reference polypeptide itself, but where the remaining amino acid sequence is usually identical to the corresponding positions in the reference polypeptide. Such deletions can occur at the amino-terminus or carboxy-terminus of the reference polypeptide, or alternatively both.

A fragment can also be a "functional fragment," in which case the fragment retains some or all of the activity of the reference polypeptide as described herein. For example, in some embodiments, a functional fragment of a cholera toxin B subunit polypeptide can refer to a polypeptide in which amino acid residues have been deleted as compared to the full-length cholera toxin B subunit polypeptide, but which retains some or all of the ability of the full-length cholera toxin B subunit polypeptide to bind to a GM1 ganglioside and/or some or all of the ability of the full-length cholera toxin B subunit polypeptide to attach to a glycan.

The terms "modified amino acid," "modified polypeptide," and "variant" are used herein to refer to an amino acid sequence that is different from the reference polypeptide by one or more amino acids, e.g., one or more amino acid substitutions or additions. A variant of a reference polypeptide also refers to a variant of a fragment of the reference polypeptide, for example, a fragment wherein one or more amino acid substitutions have been made relative to the reference polypeptide. A variant can also be a "functional variant," in which the variant retains some or all of the activity of the reference protein as described herein. For example, in some embodiments, the cholera toxin B subunit variant polypeptides described herein include amino acid sequences in which one or more amino acids have been added and/or replaced, but which nonetheless retain and/or enhance some or all of the ability of the full-length cholera toxin B subunit polypeptide to bind to a GM1 ganglioside and/or some or all of the ability of the full-length cholera toxin B subunit polypeptide to attach to a glycan.

As noted, in some embodiments of the presently-disclosed subject matter, an isolated polypeptide is provided that comprises a cholera toxin B subunit variant polypeptide having one or more modifications to increase the expression of the polypeptide in a plant cell. In some embodiments, the one or more modifications to the cholera toxin B subunit variant polypeptide include an endoplasmic reticulum retention signal having the amino acid sequence KDEL (SEQ ID NO: 31). In some embodiments, the KDEL sequence is linked to the cholera toxin by a two amino acid linker to comprise, in some embodiments, the signal: SEKDEL (SEQ ID NO: 30). In some embodiments, the cholera toxin B subunit variant polypeptide comprises the amino acid sequence of SEQ ID NO: 4, SEQ ID NO: 6, or SEQ ID NO: 25.

In some embodiments of the presently-disclosed polypeptides, the one or more modifications to the cholera toxin B subunit variant polypeptide include the addition (e.g., an addition at the N-terminal of the cholera toxin B subunit variant polypeptide) of a secretory signal peptide capable of transferring or translocating the cholera toxin B subunit peptide such that the cholera toxin B subunit variant polypeptides is accumulated in a particular location in a plant tissue, such as in the apoplasts of plant cells. In some embodiments, the secretor signal peptide is selected from the group consisting of a rice (e.g., *Oryza sativa*) alpha-amylase secretory signal peptide (e.g., SEQ ID NO: 18), a

*Nicotiana plumbagenifolia* calreticulin secretory signal peptide (e.g., SEQ ID NO: 20), an apple (e.g., *Malus domestica*) pectinase secretory signal peptide (e.g., SEQ ID NO: 22), and a barley (*Hordeum vulgare*) alpha-amylase secretory signal peptide (e.g., SEQ ID NO: 24). In some embodiments, the secretory signal peptide has an amino acid sequence selected from the group consisting of SEQ ID NOS: 18, 20, 22, and 24. In some embodiments, the secretory signal peptide comprises a rice alpha-amylase secretory signal peptide, such as the rice alpha-amylase secretory signal peptide of SEQ ID NO: 18.

In some embodiments, an isolated cholera toxin B subunit variant polypeptide is provided that comprises a cholera toxin B subunit variant linked to a secretory signal peptide, such as those described herein above, and an endoplasmic reticulum retention signal. In some embodiments, the variant polypeptide comprises an amino acid sequence selected from the group consisting of SEQ ID NOS: 26-29.

With further regard to the polypeptides of the presently-disclosed subject matter, in some embodiments, a cholera toxin B subunit variant polypeptide includes one or more mutations so as to include a plurality of N-linked glycosylation sequons (i.e., Asn-X-Ser or Asn-X-Thr sequences) in the variant polypeptide sequences and thereby provide a mechanism to display multiple N-linked H-Man glycans and mimic a virus-like carbohydrate cluster. In some embodiments, about 1, about 2, about 3, about 4, about, 5, about 6, about 7, about 8, about 9, or about 10 N-linked glycosylation sequons are included in an exemplary cholera toxin B subunit variant polypeptide of the presently-disclosed subject matter. In some embodiments, a cholera toxin B subunit variant polypeptide is provided that comprises 2 N-linked glycosylation sequons, such as, in some embodiments, a cholera toxin B subunit variant polypeptide having the amino acid sequence of SEQ ID NO: 8 or SEQ ID NO: 10. In other embodiments, a cholera toxin B subunit variant polypeptide is provided that comprises 3 N-linked glycosylation sequons, such as, in some embodiments, a cholera toxin B subunit variant polypeptide having the amino acid sequence of SEQ ID NO: 12 or SEQ ID NO: 14. In some embodiments, the polypeptide comprises two or more N-linked glycosylation sequons, such as, in some embodiments, the polypeptides of SEQ ID NO: 8, SEQ ID NO: 10, SEQ ID NO: 12, or SEQ ID NO: 14.

Further provided, in some embodiments of the presently-disclosed subject matter are pharmaceutical compositions. In some embodiments, a pharmaceutical composition is provided that comprises a cholera toxin B subunit variant polypeptide of the presently-disclosed subject matter and a pharmaceutically-acceptable vehicle, carrier, or excipient.

With regard to the pharmaceutically-acceptable vehicle, carrier, or excipient suitable for use with the polypeptides of the presently-disclosed subject matter, solid formulations of the compositions for oral administration can contain suitable carriers or excipients, such as corn starch, gelatin, lactose, acacia, sucrose, microcrystalline cellulose, kaolin, mannitol, dicalcium phosphate, calcium carbonate, sodium chloride, or alginic acid. Disintegrators that can be used include, but are not limited to, microcrystalline cellulose, corn starch, sodium starch glycolate, and alginic acid. Tablet binders that can be used include acacia, methylcellulose, sodium carboxymethylcellulose, polyvinylpyrrolidone, hydroxypropyl methylcellulose, sucrose, starch, and ethylcellulose. Lubricants that can be used include magnesium stearates, stearic acid, silicone fluid, talc, waxes, oils, and colloidal silica. Further, the solid formulations can be uncoated or they can be coated by known techniques to delay disintegration and absorption in the gastrointestinal tract and thereby provide a sustained/extended action over a longer period of time. For example, glyceryl monostearate or glyceryl distearate can be employed to provide a sustained-/extended-release formulation. Numerous techniques for formulating sustained release preparations are known to those of ordinary skill in the art and can be used in accordance with the present invention, including the techniques described in the following references: U.S. Pat. Nos. 4,891,223; 6,004,582; 5,397,574; 5,419,917; 5,458,005; 5,458,887; 5,458,888; 5,472,708; 6,106,862; 6,103,263; 6,099,862; 6,099,859; 6,096,340; 6,077,541; 5,916,595; 5,837,379; 5,834,023; 5,885,616; 5,456,921; 5,603,956; 5,512,297; 5,399,362; 5,399,359; 5,399,358; 5,725,883; 5,773,025; 6,110,498; 5,952,004; 5,912,013; 5,897,876; 5,824,638; 5,464,633; 5,422,123; and 4,839,177; and WO 98/47491, each of which is incorporated herein by this reference.

Furthermore, liquid formulations of the compositions for oral administration can be prepared in water or other aqueous vehicles, and can contain various suspending agents such as methylcellulose, alginates, tragacanth, pectin, kelgin, carrageenan, acacia, polyvinylpyrrolidone, and include solutions, emulsions, syrups, and elixirs containing, together with the active components of the composition, wetting agents, sweeteners, and coloring and flavoring agents.

Various liquid and powder formulations can also be prepared by conventional methods for inhalation into the lungs of the subject to be treated. For example, the compositions can be conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide or other suitable gas. Capsules and cartridges of, for example, gelatin for use in an inhaler or insufflator may be formulated containing a powder mix of the desired compound and a suitable powder base such as lactose or starch.

Injectable formulations of the compositions can contain various carriers such as vegetable oils, dimethylacetamide, dimethylformamide, ethyl lactate, ethyl carbonate, isopropyl myristate, ethanol, polyols (glycerol, propylene glycol, liquid polyethylene glycol), and the like. For intravenous injections, water soluble versions of the compositions can be administered by the drip method, whereby a formulation including a pharmaceutical composition of the presently-disclosed subject matter and a physiologically-acceptable excipient is infused. Physiologically-acceptable excipients can include, for example, 5% dextrose, 0.9% saline, Ringer's solution or other suitable excipients. Intramuscular preparations, e.g., a sterile formulation of a suitable soluble salt form of the compositions, can be dissolved and administered in a pharmaceutical excipient such as Water-for-Injection, 0.9% saline, or 5% glucose solution. A suitable insoluble form of the compositions can be prepared and administered as a suspension in an aqueous base or a pharmaceutically-acceptable oil base, such as an ester of a long chain fatty acid, (e.g., ethyl oleate).

In addition to the formulations described above, the compositions of the presently-disclosed subject matter can also be formulated as rectal compositions, such as suppositories or retention enemas, e.g., containing conventional suppository bases such as cocoa butter or other glycerides. Further, the compositions can also be formulated as a depot preparation by combining the compositions with suitable polymeric or hydrophobic materials (for example as an emulsion in an acceptable oil) or ion exchange resins, or as sparingly soluble derivatives, for example, as a sparingly soluble salt.

In some embodiments of the present invention, the compositions of the present invention may be incorporated as part of a nanoparticle. A "nanoparticle" within the scope of the presently-disclosed subject matter is meant to include particles at the single molecule level as well as those aggregates of particles that exhibit microscopic properties. Methods of using and making a nanoparticle that incorporates a compound of interest are known to those of ordinary skill in the art and can be found following references: U.S. Pat. Nos. 6,395,253, 6,387,329, 6,383,500, 6,361,944, 6,350,515, 6,333,051, 6,323,989, 6,316,029, 6,312,731, 6,306,610, 6,288,040, 6,272,262, 6,268,222, 6,265,546, 6,262,129, 6,262,032, 6,248,724, 6,217,912, 6,217,901, 6,217,864, 6,214,560, 6,187,559, 6,180,415, 6,159,445, 6,149,868, 6,121,005, 6,086,881, 6,007,845, 6,002,817, 5,985,353, 5,981,467, 5,962,566, 5,925,564, 5,904,936, 5,856,435, 5,792,751, 5,789,375, 5,770,580, 5,756,264, 5,705,585, 5,702,727, and 5,686,113, each of which is incorporated herein by this reference.

A topical formulation (e.g., a semi-solid ointment formulation) can also be provided and can contain a desired concentration of the active ingredient (e.g., a polypeptide of the presently-disclosed subject matter) in a carrier such as a pharmaceutical cream base. Various formulations for topical use include drops, tinctures, lotions, creams, solutions, and ointments containing the active ingredient and various supports and vehicles. The optimal percentage of the therapeutic agent in each pharmaceutical formulation varies according to the formulation itself and the therapeutic effect desired in the specific pathologies and correlated therapeutic.

In some embodiments, the pharmaceutical compositions of the presently-disclosed subject matter are in the form of a vaccine. In some embodiments, such immunogenic compositions and vaccines according to the presently disclosed subject matter can comprise or consist essentially of one or more adjuvants. Suitable adjuvants for use in the practice of the presently-disclosed subject matter include, but are not limited to: (1) polymers of acrylic or methacrylic acid, maleic anhydride and alkenyl derivative polymers, (2) immunostimulating sequences (ISS), such as oligodeoxyribonucleotide sequences having one ore more non-methylated CpG units (Klinman et al., Proc. Natl. Acad. Sci., USA, 1996, 93, 2879-2883; WO98/16247), (3) an oil in water emulsion, such as the SPT emulsion described on p. 147 of "Vaccine Design, The Subunit and Adjuvant Approach" published by M. Powell, M. Newman, Plenum Press 1995, and the emulsion MF59 described on p 183 of the same work, (4) cation lipids containing a quaternary ammonium salt, (5) cytokines, (6) aluminum hydroxide or aluminum phosphate or (7) other adjuvants such as toll-like receptor ligands or those discussed in any document cited and incorporated by reference into the instant application, or (8) any combinations or mixtures thereof.

The oil in water emulsion (3), which can be particularly appropriate for viral vaccines, can be based on: light liquid paraffin oil (European pharmacopoeia type), isoprenoid oil such as squalane, squalene, oil resulting from the oligomerization of alkenes, e.g. isobutene or decene, esters of acids or alcohols having a straight-chain alkyl group, such as vegetable oils, ethyl oleate, propylene glycol, di(caprylate/caprate), glycerol tri(caprylate/caprate) and propylene glycol dioleate, or esters of branched, fatty alcohols or acids, especially isostearic acid esters. The oil can be used in combination with emulsifiers to form an emulsion. The emulsifiers can be nonionic surfactants, such as: esters of, on the one hand, sorbitan, mannide (e.g. anhydromannitol oleate), glycerol, polyglycerol or propylene glycol and, on the other hand, oleic, isostearic, ricinoleic or hydroxystearic acids, the esters being optionally ethoxylated, or polyoxypropylene-polyoxyethylene copolymer blocks, such as Pluronic® (BASF Corporation, NJ), e.g., L121.

Among the type (1) adjuvant polymers, in some embodiments, the polymers are polymers of crosslinked acrylic or methacrylic acid, including those crosslinked by polyalkenyl ethers of sugars or polyalcohols. These compounds are known under the name carbomer (Pharmeuropa, vol. 8, no. 2, June 1996). One skilled in the art can also refer to U.S. Pat. No. 2,909,462, which provides such acrylic polymers crosslinked by a polyhydroxyl compound having at least three hydroxyl groups, preferably no more than eight such groups, the hydrogen atoms of at least three hydroxyl groups being replaced by unsaturated, aliphatic radicals having at least two carbon atoms. The preferred radicals are those containing 2 to 4 carbon atoms, e.g. vinyls, allyls and other ethylenically unsaturated groups. The unsaturated radicals can also contain other substituents, such as methyl. Products sold under the name CARBOPOL™ (BF Goodrich, Ohio, USA) are, in some embodiments, especially suitable, as such products are crosslinked by allyl saccharose or by allyl pentaerythritol. Among them, reference is made to CARBOPOL™ 974P, 934P and 971 P. As to the maleic anhydride-alkenyl derivative copolymers, in some embodiments, the derivative copolymers are EMA polymers, which are straight-chain or crosslinked ethylene-maleic anhydride copolymers that are, for example, crosslinked by divinyl ether. Reference is also made to J. Fields et al., Nature 186: 778-780, Jun. 4, 1960.

Still further provided, in some embodiments of the presently-disclosed subject matter, are isolated nucleic acids. In some embodiments, isolated nucleic acid sequences are provided that encode the cholera toxin subunit B variant polypeptides of the presently-disclosed subject matter. In some embodiments, a nucleic acid is provided that comprises the nucleic acid sequence of SEQ ID NO: 3, SEQ ID NO: 5, SEQ ID NO: 7, SEQ ID NO: 9, SEQ ID NO: 11, or SEQ ID NO: 13. In some embodiments, a nucleic acid sequence is provided that comprises the nucleic acid sequence of SEQ ID NO: 15. In some embodiments, additional nucleic acid sequences are provided wherein the nucleic acid sequences are derived from a *Vibrio cholerae* cholera toxin B subunit gene and used to produce a cholera toxin B subunit variant polypeptide of the presently-disclosed subject matter.

The term "gene" is used broadly to refer to any segment of DNA associated with a biological function. Thus, genes include, but are not limited to, coding sequences and/or the regulatory sequences required for their expression. Genes can also include non-expressed DNA segments that, for example, form recognition sequences for a polypeptide. Genes can be obtained from a variety of sources, including cloning from a source of interest or synthesizing from known or predicted sequence information, and can include sequences designed to have desired parameters.

The term "nucleic acid" refers to deoxyribonucleotides or ribonucleotides and polymers thereof in either single- or double-stranded form. Unless specifically limited, the term encompasses nucleic acids containing known analogues of natural nucleotides that have similar binding properties as the reference nucleic acid and are metabolized in a manner similar to naturally-occurring nucleotides. Unless otherwise indicated, a particular nucleic acid sequence also implicitly encompasses conservatively modified variants thereof (e.g., degenerate codon substitutions) and complementary sequences and as well as the sequence explicitly indicated.

The term "isolated", when used in the context of an isolated nucleic acid molecule or an isolated polypeptide, is a nucleic acid molecule or polypeptide that, by the hand of man, exists apart from its native environment and is therefore not a product of nature. An isolated nucleic acid molecule or polypeptide can exist in a purified form or can exist in a non-native environment such as, for example, in a transgenic host cell.

The term "degenerate variant" refers to a nucleic acid having a residue sequence that differs from a reference nucleic acid by one or more degenerate codon substitutions. Degenerate codon substitutions can be achieved by generating sequences in which the third position of one or more selected (or all) codons is substituted with mixed base and/or deoxyinosine residues (Batzer et al. (1991) *Nucleic Acid Res* 19:5081; Ohtsuka et al. (1985) *J Biol Chem* 260:2605 2608; Rossolini et al. (1994) *Mol Cell Probes* 8:91 98).

In some embodiments, an isolated nucleic acid sequence is provided that selectively hybridizes to the nucleic acid sequence of SEQ ID NO: 3, SEQ ID NO: 5, SEQ ID NO: 7, SEQ ID NO: 9, SEQ ID NO: 11, SEQ ID NO: 13, or SEQ ID NO: 15. The term "selectively hybridize" as used herein refers to the ability of a nucleic acid sequence to hybridize to a target polynucleotide (e.g., a polynucleotide of SEQ ID NO: 3, SEQ ID NO: 5, SEQ ID NO: 7, SEQ ID NO: 9, SEQ ID NO: 11, SEQ ID NO: 13, or SEQ ID NO: 15) with specificity. Thus, the nucleic acid sequence comprises a polynucleotide sequence that is complementary, or essentially complementary, to at least a portion of the target polynucleotide sequence. For example, in some embodiments, the nucleic acid sequence that selectively hybridizes to the sequence of SEQ ID NO: 3 is complementary to the sequence of SEQ ID NO: 3. Nucleic acid sequences which are "complementary" are those which are base-pairing according to the standard Watson-Crick complementarity rules. As used herein, the term "complementary sequences" means nucleic acid sequences which are substantially complementary, as can be assessed by the same nucleotide comparison set forth above, or as defined as being capable of hybridizing to the nucleic acid segment in question under relatively stringent conditions such as those described herein. A particular example of a contemplated complementary nucleic acid segment is an antisense oligonucleotide. With regard to the nucleic acid sequences disclosed herein as selectively hybridizing to the sequence of SEQ ID NO: 3, SEQ ID NO: 5, SEQ ID NO: 7, SEQ ID NO: 9, SEQ ID NO: 11, SEQ ID NO: 13, or SEQ ID NO: 15, the hybridizing nucleic acid sequence need not necessarily be completely complementary to the nucleic acid sequence of SEQ ID NO: 3, SEQ ID NO: 5, SEQ ID NO: 7, SEQ ID NO: 9, SEQ ID NO: 11, SEQ ID NO: 13, or SEQ ID NO: 15 along the entire length of the target polynucleotide so long as the hybridizing nucleic acid sequence can bind the nucleic acid of SEQ ID NO: 3, SEQ ID NO: 5, SEQ ID NO: 7, SEQ ID NO: 9, SEQ ID NO: 11, SEQ ID NO: 13, or SEQ ID NO: 15 with specificity. In some embodiments, the nucleic acid sequences that selectively hybridize to the sequence of SEQ ID NO: 3, SEQ ID NO: 5, SEQ ID NO: 7, SEQ ID NO: 9, SEQ ID NO: 11, SEQ ID NO: 13, or SEQ ID NO: 15 are about 80%, about 85%, about 90%, about 95%, about 98%, or about 100% complementary to the sequence of SEQ ID NO: 3, SEQ ID NO: 5, SEQ ID NO: 7, SEQ ID NO: 9, SEQ ID NO: 11, SEQ ID NO: 13, or SEQ ID NO: 15, respectively.

Nucleic acid hybridization will be affected by such conditions as salt concentration, temperature, or organic solvents, in addition to the base composition, length of the complementary strands, and the number of nucleotide base mismatches between the hybridizing nucleic acids, as will be readily appreciated by those skilled in the art. Stringent temperature conditions will generally include temperatures in excess of 30° C., typically in excess of 37° C., and preferably in excess of 45° C. Stringent salt conditions will ordinarily be less than 1,000 mM, typically less than 500 mM, and preferably less than 200 mM. For example, in some embodiments, nucleic acid hybridization can be performed at 60° C. with 0.1× sodium citrate-sodium chloride (SSC) and 0.1% sodium dodecyl sulfate (SDS). However, the combination of parameters is much more important than the measure of any single parameter. (See, e.g., Wetmur & Davidson, 1968). Determining appropriate hybridization conditions to identify and/or isolate sequences containing high levels of homology is well known in the art. (See, e.g., Sambrook, et al., 1989).

Further provided, in some embodiments, are expression vectors comprising the nucleic acid molecules of the presently-disclosed subject matter operably linked to an expression cassette. The term "vector" is used herein to refer to any vehicle that is capable of transferring a nucleic acid sequence into another cell. For example, vectors which can be used in accordance with the presently-disclosed subject matter include, but are not limited to, plasmids, cosmids, bacteriophages, or viruses, which can be transformed by the introduction of a nucleic acid sequence of the presently-disclosed subject matter. Such vectors are well known to those of ordinary skill in the art.

In some embodiments, the nucleic acids of the presently-disclosed subject matter are operably linked to an expression cassette. The terms "associated with", "operably linked", and "operatively linked" refer to two sequences that are related physically or functionally. For example, a promoter or regulatory DNA sequence is said to be "associated with" a DNA sequence that encodes an RNA or a polypeptide if the two sequences are operatively linked, or situated such that the regulator DNA sequence will affect the expression level of the coding or structural DNA sequence.

The term "expression cassette" refers to a nucleic acid molecule capable of directing expression of a particular nucleotide sequence in an appropriate host cell, comprising a promoter operatively linked to the nucleotide sequence of interest which is operatively linked to termination signals. It also typically comprises sequences required for proper translation of the nucleotide sequence. The coding region usually encodes a polypeptide of interest but can also encode a functional RNA of interest, for example antisense RNA or a non-translated RNA, in the sense or antisense direction. The expression cassette comprising the nucleotide sequence of interest can be chimeric, meaning that at least one of its components is heterologous with respect to at least one of its other components. The expression cassette can also be one that is naturally occurring but has been obtained in a recombinant form useful for heterologous expression.

The presently-disclosed subject matter also provides transgenic plant cells or plants that have been transformed with one or more of the vectors disclosed herein (i.e., a vector including a nucleic acid molecule encoding for a cholera toxin B subunit polypeptide or variant thereof). In some embodiments, a plant cell, or a progeny of the plant cell, is provided wherein the plant cell and/or its progeny is transfected with a vector of the presently-disclosed subject matter such that the cell and/or its progeny expresses the polypeptide. As used herein, the term "plant cell" is understood to mean any cell derived from a monocotyledonous or a dicotyledonous plant and capable of constituting undifferentiated tissues such as calli, differentiated tissues such as embryos, portions of monocotyledonous plants, monocotyledonous plants or seed. The term "plant" is understood to mean any differentiated multi-cellular organism capable of photosynthesis, including monocotyledons and dicotyledons. In some embodiments, the plant cell is a *Nicotiana* or tobacco plant cell, such as a *Nicotiana benthamiana* plant cell that has been transformed with a vector of the presently-disclosed subject matter.

The terms "transformed," "transgenic," and "recombinant" are used herein to refer to a cell of a host organism, such as a plant, into which a heterologous nucleic acid molecule has been introduced. The nucleic acid molecule can be stably integrated into the genome of the cell or the nucleic acid molecule can also be present as an extrachromosomal molecule. Such an extrachromosomal molecule can be auto-replicating. Transformed cells, tissues, or subjects are understood to encompass not only the end product of a transformation process, but also transgenic progeny thereof.

The terms "heterologous," "recombinant," and "exogenous," when used herein to refer to a nucleic acid sequence (e.g., a DNA sequence) or a gene, refer to a sequence that originates from a source foreign to the particular host cell or, if from the same source, is modified from its original form. Thus, a heterologous gene in a host cell includes a gene that is endogenous to the particular host cell but has been modified through, for example, the use of site-directed mutagenesis or other recombinant techniques. The terms also include non-naturally occurring multiple copies of a naturally occurring DNA sequence. Thus, the terms refer to a DNA segment that is foreign or heterologous to the cell, or homologous to the cell but in a position or form within the host cell in which the element is not ordinarily found. Similarly, when used in the context of a polypeptide or amino acid sequence, an exogenous polypeptide or amino acid sequence is a polypeptide or amino acid sequence that originates from a source foreign to the particular host cell or, if from the same source, is modified from its original form. Thus, exogenous DNA segments can be expressed to yield exogenous polypeptides.

Introduction of a nucleic acid (e.g., a nucleic acid incorporated into an appropriate vector) of the presently-disclosed subject matter into a plant cell can be performed by a variety of methods known to those of ordinary skill in the art including, but not limited to, insertion of a nucleic acid sequence of interest into an *Agrobacterium rhizogenes* Ri or *Agrobacterium tumefaciens* Ti plasmid, microinjection, electroporation, or direct precipitation. By way of providing an example, in some embodiments, transient expression of a nucleic acid sequence or gene of interest can be performed by agro-infiltration methods. In this regard, a suspension of *Agrobacterium tumefaciens* containing a nucleic acid sequence or gene of interest can be grown in culture and then vacuum-infiltrated into a plant. Once inside the tissues of the plant (e.g., the leaves of the plant), the *Agrobacterium* transforms the gene of interest to a portion of the plant cells where the gene is then transiently expressed.

As another example, transformation of a plasmid or nucleic acid of interest into a plant cell can be performed by particle gun bombardment techniques. In this regard, a suspension of plant embryos can be grown in liquid culture and then bombarded with plasmids or nucleic acids that are attached to gold particles, wherein the gold particles bound to the plasmid or nucleic acid of interest can be propelled through the membranes of the plant tissues, such as embryonic tissue. Following bombardment, the transformed embryos can then be selected using an appropriate antibiotic to generate new, clonally propagated, transformed embryogenic suspension cultures.

For additional guidance regarding methods of transforming and producing transgenic plant cells, see U.S. Pat. Nos. 4,459,355; 4,536,475; 5,464,763; 5,177,010; 5,187,073; 4,945,050; 5,036,006; 5,100,792; 5,371,014; 5,478,744; 5,179,022; 5,565,346; 5,484,956; 5,508,468; 5,538,877; 5,554,798; 5,489,520; 5,510,318; 5,204,253; 5,405,765; EP Nos. 267,159; 604,662; 672,752; 442,174; 486,233; 486,234; 539,563; 674,725; and, International Patent Application Publication Nos. WO 91/02071 and WO 95/06128, each of which is incorporated herein by this reference.

In yet further embodiments of the presently-disclosed subject matter, methods of producing a cholera toxin B subunit polypeptide are provided. In some embodiments, a method of producing a cholera toxin B subunit polypeptide is provided that comprises: transforming a plant cell with a nucleic acid encoding a cholera toxin B subunit variant polypeptide of the presently-disclosed subject matter (i.e., a cholera toxin B subunit variant polypeptide having one or more modifications to increase the expression of the polypeptide in a plant cell and/or to display one or more H-Man glycans); expressing the cholera toxin B subunit variant polypeptide in the plant cell; and purifying the cholera toxin B subunit variant polypeptide. In some embodiments, the plant cell comprises a plant cell from the genus *Nicotiana*, such as, in some embodiments, a *Nicotiana benthamiana* plant cell.

The term "purifying" as used herein in reference to the production of the cholera toxin B subunit variant polypeptide refers to methods by which the cholera toxin B subunit variant polypeptide can be isolated from unwanted materials, including contaminants, that may be found or be otherwise present in plant tissue expressing an exemplary cholera toxin B subunit variant polypeptide of the presently-disclosed subject matter. Such purification methods include, but are not limited, to: protein precipitation including immunoprecipitation, ultracentrifugation, and chromatography including size-exclusion chromatography, hydrophobic interaction chromatography, ion exchange chromatography, and affinity chromatography, immunoaffinity chromatography, high-performance liquid chromatography, and the like.

As one example of the purification of a cholera toxin B subunit variant polypeptide of the presently-disclosed subject matter, in some embodiments, the purification of a cholera toxin B subunit variant polypeptide is accomplished by first homogenizing transgenic plant tissue (e.g., leaf tissue) of the presently-disclosed subject matter to obtain plant tissue extracts. These tissue extracts are then clarified and the pH of the extracts is adjusted to about 5 to about 8 before performing liquid chromatography to obtain the variant polypeptides. In some embodiments, after the initial chromatography steps are performed, an additional chromatography step is performed (e.g., using a hydroxyapatite column) followed by a phase separation step to remove endotoxins to obtain the purified protein. It has been determined, however, that in some embodiments, a variant polypeptide of the presently-disclosed subject matter that is produced in plants can be highly-purified to, in some embodiments, a purification level of about 80%, about 85%, about 90%, about 95%, about 96%, about 97%, about 98%, or about 99% without the use of a second chromatographic step and/or without the use of an endotoxin removal step.

In some embodiments of the presently-disclosed subject matter, a method of isolating a cholera toxin B subunit polypeptide or variant thereof from a plant tissue is provided that comprises: obtaining a plant cell expressing a cholera toxin B subunit variant polypeptide of the presently-disclosed subject matter; extracting the cholera toxin B subunit variant polypeptide from the plant cell; and purifying the cholera toxin B subunit variant from the plant cell. In some embodiments, the step of extracting the cholera toxin B subunit polypeptide or variant thereof from the plant cell comprises homogenizing the plant tissue in an aqueous buffer having an acidic pH of about 4, about 5, or about 6. In some embodiments, the pH of the buffer is about 5. In some embodiments, the buffer has a basic pH, such as a pH of about 8. In some embodiments, the step of purifying the cholera toxin B subunit polypeptide or variant thereof from the plant cell comprises purifying the polypeptide or variant thereof using chromatography.

In further embodiments of the presently-disclosed subject matter, methods for eliciting an immune response in a subject are provided. In some embodiments, a method for eliciting an immune response in a subject is provided that comprises administering to a subject an effective amount of a cholera toxin B subunit variant polypeptide of the presently-disclosed subject matter. In some embodiments, administering an effective amount of the cholera toxin B subunit variant polypeptide increases an amount of IgG, IgA, IgM, and/or other immunglobulins, and effector or regulatory T cells in a subject. In some embodiments, administering an effective amount of the cholera toxin B subunit variant polypeptide increases an amount of IgG, IgA, IgM, effector T cells, regulatory T cells, or combinations thereof in a subject.

Various methods known to those skilled in the art can be used to determine an increase in the amount of IgG, IgA, IgM, other immunoglobulins, and/or T cells in a subject. For example, in certain embodiments, the amounts of expression of the immunoglobulins and the activation of the T cells in a subject can be determined by probing for mRNA of the gene encoding the immunoglobulin in a biological sample obtained from the subject (e.g., a tissue sample, a urine sample, a saliva sample, a blood sample, a serum sample, a plasma sample, or sub-fractions thereof) using any RNA identification assay known to those skilled in the art. Briefly, RNA can be extracted from the sample, amplified, converted to cDNA, labeled, and allowed to hybridize with probes of a known sequence, such as known RNA hybridization probes immobilized on a substrate, e.g., array, or microarray, or quantitated by real time PCR (e.g., quantitative real-time PCR, such as available from Bio-Rad Laboratories, Hercules, Calif.). Because the probes to which the nucleic acid molecules of the sample are bound are known, the molecules in the sample can be identified. In this regard, DNA probes for one or more of the mRNAs encoded by the immunoglobulins or T cell activation marker molecules can be immobilized on a substrate and provided for use in practicing a method in accordance with the present invention.

With further regard to determining levels of the immunoglobulins in samples, mass spectrometry and/or immunoassay devices and methods can be used to measure the immunoglobulins in samples, although other methods can also be used and are well known to those skilled in the art. See, e.g., U.S. Pat. Nos. 6,143,576; 6,113,855; 6,019,944; 5,985,579; 5,947,124; 5,939,272; 5,922,615; 5,885,527; 5,851,776; 5,824,799; 5,679,526; 5,525,524; and 5,480,792, each of which is hereby incorporated by reference in its entirety. Immunoassay devices and methods can utilize labeled molecules in various sandwich, competitive, or non-competitive assay formats, to generate a signal that is related to the presence or amount of an analyte of interest. Additionally, certain methods and devices, such as biosensors and optical immunoassays, can be employed to determine the presence or amount of analytes without the need for a labeled molecule. See, e.g., U.S. Pat. Nos. 5,631,171; and 5,955,377, each of which is hereby incorporated by reference in its entirety.

Any suitable immunoassay can be utilized, for example, enzyme-linked immunoassays (ELISA), radioimmunoassays (RIAs), competitive binding assays, and the like. Specific immunological binding of the immunoglobulins can be detected directly or indirectly. Direct labels include fluorescent or luminescent tags, metals, dyes, radionucleotides, and the like, attached to the antibody. Indirect labels include various enzymes well known in the art, such as alkaline phosphatase, horseradish peroxidase and the like.

The use of immobilized antibodies or fragments thereof specific for the immunoglobulins is also contemplated by the presently-disclosed subject matter. The antibodies can be immobilized onto a variety of solid supports, such as magnetic or chromatographic matrix particles, the surface of an assay plate (such as microtiter wells), pieces of a solid substrate material (such as plastic, nylon, paper), and the like. An assay strip can be prepared by coating the antibody or a plurality of antibodies in an array on a solid support. This strip can then be dipped into the test biological sample and then processed quickly through washes and detection steps to generate a measurable signal, such as for example a colored spot.

Mass spectrometry (MS) analysis can be used, either alone or in combination with other methods (e.g., immunoassays), to determine the presence and/or quantity of an inflammatory molecule in a subject. Exemplary MS analyses that can be used in accordance with the present invention include, but are not limited to: liquid chromatography-mass spectrometry (LC-MS); matrix-assisted laser desorption/ionization time-of-flight MS analysis (MALDI-TOF-MS), such as for example direct-spot MALDI-TOF or liquid chromatography MALDI-TOF mass spectrometry analysis; electrospray ionization MS (ESI-MS), such as for example liquid chromatography (LC) ESI-MS; and surface enhanced laser desorption/ionization time-of-flight mass spectrometry analysis (SELDI-TOF-MS). Each of these types of MS analysis can be accomplished using commercially-available spectrometers, such as, for example, triple quadropole mass spectrometers. Methods for utilizing MS analysis to detect the presence and quantity of peptides, such as immunoglobulins, in biological samples are known in the art. See, e.g., U.S. Pat. Nos. 6,925,389; 6,989,100; and 6,890,763 for further guidance, each of which are incorporated herein by this reference.

With regard to the various methods of eliciting an immune response described herein, although certain embodiments of the methods only call for a qualitative assessment (e.g., the presence or absence of the expression of an immunoglobulin), other embodiments of the methods call for a quantitative assessment (e.g., an amount of increase in a level of immunoglobulins, T cells, or both in a subject). Such quantitative assessments can be made, for example, using one of the above mentioned methods, as will be understood by those skilled in the art.

The skilled artisan will also understand that measuring an increase in the amount of a certain feature (e.g., IgA levels) in a subject is a statistical analysis. For example, a reduction in an amount of IgA levels in a subject can be compared to control level of IgA, and an amount of IgA of more than the control level can be indicative of an increase in the amount of IgA, as evidenced by a level of statistical significance. Statistical significance is often determined by comparing two or more populations, and determining a confidence interval and/or a p value. See, e.g., Dowdy and Wearden, Statistics for Research, John Wiley & Sons, New York, 1983, incorporated herein by reference in its entirety. Preferred confidence intervals of the present subject matter are 90%, 95%, 97.5%, 98%, 99%, 99.5%, 99.9% and 99.99%, while preferred p values are 0.1, 0.05, 0.025, 0.02, 0.01, 0.005, 0.001, and 0.0001.

For administration of a therapeutic composition as disclosed herein (e.g., a composition comprising a cholera toxin B subunit variant polypeptide of the presently-disclosed subject matter and a pharmaceutically-acceptable vehicle, carrier, or excipient), conventional methods of extrapolating human dosage based on doses administered to a murine animal model can be carried out using the conversion factor for converting the mouse dosage to human dosage: Dose Human per kg=Dose Mouse per kg×12 (Freireich, et al., (1966) Cancer Chemother Rep. 50:219-244). Drug doses can also be given in milligrams per square meter of body surface area because this method rather than body weight achieves a good correlation to certain metabolic and excretionary functions. Moreover, body surface area can be used as a common denominator for drug dosage in adults and children as well as in different animal species as described by Freireich, et al. (Freireich et al., (1966) Cancer Chemother Rep. 50:219-244). Briefly, to express a mg/kg dose in any given species as the equivalent mg/sq m dose, multiply the dose by the appropriate km factor. In an adult human, 100 mg/kg is equivalent to 100 mg/kg×37 kg/sq m=3700 mg/m2.

Suitable methods for administering a therapeutic composition in accordance with the methods of the presently-disclosed subject matter include, but are not limited to, systemic administration, parenteral administration (including intravascular, intramuscular, intraarterial administration), oral delivery, topical administration, buccal delivery, rectal delivery, vaginal delivery, subcutaneous administration, intraperitoneal administration, inhalation, intratracheal installation, surgical implantation, transdermal delivery, local injection, and hyper-velocity injection/bombardment. Where applicable, continuous infusion can enhance drug accumulation at a target site (see, e.g., U.S. Pat. No. 6,180,082). In some embodiments, such as those which include a pharmaceutical composition comprising a cholera toxin B subunit variant polypeptide of the presently-disclosed subject matter, the pharmaceutical composition can be administered orally to thereby elicit an immune response.

Regardless of the route of administration, the compounds of the presently-disclosed subject matter are typically administered in amount effective to achieve the desired response. As used herein, the terms "effective amount" and "therapeutically effective amount" refer to an amount of the therapeutic composition (e.g., a composition comprising a cholera toxin B subunit variant polypeptide of the presently-disclosed subject matter, and a pharmaceutically-acceptable vehicle, carrier, or excipient) sufficient to produce a measurable biological response (e.g., an increase in levels of IgA). Actual dosage levels of active ingredients in a therapeutic composition of the presently-disclosed subject matter can be varied so as to administer an amount of the active polypeptide(s) that is effective to achieve the desired therapeutic response for a particular subject and/or application. Of course, the effective amount in any particular case will depend upon a variety of factors including the activity of the therapeutic composition, formulation, the route of administration, combination with other drugs or treatments, severity of the condition being treated, and the physical condition and prior medical history of the subject being treated. Preferably, a minimal dose is administered, and the dose is escalated in the absence of dose-limiting toxicity to a minimally effective amount. Determination and adjustment of a therapeutically effective dose, as well as evaluation of when and how to make such adjustments, are known to those of ordinary skill in the art.

For additional guidance regarding formulation and dose, see U.S. Pat. Nos. 5,326,902 and 5,234,933; PCT International Publication No. WO 93/25521; Berkow, et al., (1997) The Merck Manual of Medical Information, Home ed. Merck Research Laboratories, Whitehouse Station, N.J.; Goodman, et al., (2006) Goodman & Gilman's the Pharmacological Basis of Therapeutics, 11th ed. McGraw-Hill Health Professions Division, New York; Ebadi. (1998) CRC Desk Reference of Clinical Pharmacology. CRC Press, Boca Raton, Fla.; Katzung, (2007) Basic & Clinical Pharmacology, 10th ed. Lange Medical Books/McGraw-Hill Medical Pub. Division, New York; Remington, et al., (1990) Remington's Pharmaceutical Sciences, 18th ed. Mack Pub. Co., Easton, Pa.; Speight, et al., (1997) Avery's Drug Treatment: A Guide to the Properties, Choice, Therapeutic Use and Economic Value of Drugs in Disease Management, 4th ed. Adis International, Auckland/Philadelphia; and Duch, et al., (1998) Toxicol. Lett. 100-101:255-263, each of which are incorporated herein by reference.

As used herein, the term "subject" includes both human and animal subjects. Thus, veterinary therapeutic uses are provided in accordance with the presently-disclosed subject matter. As such, the presently-disclosed subject matter provides for the treatment of mammals such as humans, as well as those mammals of importance due to being endangered, such as Siberian tigers; of economic importance, such as animals raised on farms for consumption by humans; and/or animals of social importance to humans, such as animals kept as pets or in zoos. Examples of such animals include but are not limited to: carnivores such as cats and dogs; swine, including pigs, hogs, and wild boars; ruminants and/or ungulates such as cattle, oxen, sheep, giraffes, deer, goats, bison, and camels; and horses. Also provided is the treatment of birds, including the treatment of those kinds of birds that are endangered and/or kept in zoos, as well as fowl, and more particularly domesticated fowl, i.e., poultry, such as turkeys, chickens, ducks, geese, guinea fowl, and the like, as they are also of economic importance to humans. Thus, also provided is the treatment of livestock, including, but not limited to, domesticated swine, ruminants, ungulates, horses (including race horses), poultry, and the like.

The practice of the presently-disclosed subject matter can employ, unless otherwise indicated, conventional techniques of cell biology, cell culture, molecular biology, transgenic biology, microbiology, recombinant DNA, and immunology, which are within the skill of the art. Such techniques are explained fully in the literature. See, e.g., Molecular Cloning A Laboratory Manual (1989), 2nd Ed., ed. by Sambrook, Fritsch and Maniatis, eds., Cold Spring Harbor Laboratory Press, Chapters 16 and 17; U.S. Pat. No. 4,683,195; DNA Cloning, Volumes I and II, Glover, ed., 1985; Polynucleotide Synthesis, M. J. Gait, ed., 1984; Nucleic Acid Hybridization, D. Hames & S. J. Higgins, eds., 1984; Transcription and Translation, B. D. Hames & S. J. Higgins, eds., 1984; Culture Of Animal Cells, R. I. Freshney, Alan R. Liss, Inc., 1987; Immobilized Cells And Enzymes, IRL Press, 1986;

Perbal (1984), A Practical Guide To Molecular Cloning; See Methods In Enzymology (Academic Press, Inc., N.Y.); Gene Transfer Vectors For Mammalian Cells, J. H. Miller and M. P. Calos, eds., Cold Spring Harbor Laboratory, 1987; Methods In Enzymology, Vols. 154 and 155, Wu et al., eds., Academic Press Inc., N.Y.; Immunochemical Methods In Cell And Molecular Biology (Mayer and Walker, eds., Academic Press, London, 1987; Handbook Of Experimental Immunology, Volumes I-IV, D. M. Weir and C. C. Blackwell, eds., 1986.

The presently-disclosed subject matter is further illustrated by the following specific but non-limiting examples.

EXAMPLES

Example 1

Expression of Cholera Toxin B Subunit Variants in *Nicotiana benthamiana*

To evaluate the expression of cholera toxin B subunit variants in plant cells in an effort to develop a cholera toxin B subunit variant production platform, deconstructed virus vectors were designed to allow for the transient expression of a recombinant (r) CTB in *Nicotiana benthamiana*. Briefly, a "deconstructed" tobamovirus replicon system [1, 2] (magnICON®; Icon Genetics GmbH, Halle/Saale, Germany) was used to express a cholera toxin B subunit variant polypeptide (SEQ ID NO: 16) in *N. benthamiana*, which included the plant-expression-optimized synthetic CTB gene (corresponding to nucleotides 64 to 372 of GENBANK® accession no. AY475128) containing a C-terminal endoplasmic reticulum (ER) retention signal attached to a two amino acid linker sequence (SEKDEL; SEQ ID NO: 30) [3] that was sub-cloned into the magnICON vector pICH115991 using NcoI and Sad endonuclease restriction sites to generate pNM134. For expression of the cholera toxin B subunit variant polypeptide with the original *Vibrio cholerae* N-terminal secretory signal peptide, the nucleic acid sequence (SEQ ID NO: 15) encoding the above-mentioned cholera toxin B subunit variant polypeptide (SEQ ID NO: 16) was used as a template for PCR. A 5' oligonucleotide corresponding to the *V. cholerae* secretory signal sequence (GENBANK® accession no. U25679, nucleotide 1 to 63) and the 5' nucleotide region of the CTB gene and a 3' oligonucleotide corresponding to the 3' nucleotide region of the CTB gene were used to amplify the *V. cholerae* secretory signal +CTB+SEKDEL-coding sequence (SEQ ID NO: 15). The resulting PCR product was sub-cloned into pIHC11599 using NcoI and Sad endonuclease restriction sites to generate pNM47. The in frame DNA sequences were then confirmed at the University of Louisville Microarray Core Facility. For expression of further cholera toxin B subunit variant polypeptides including secretory signals other than the original *V. cholerae* peptide, as described further below, the 5' provectors pICH20155, pICH20188, pICH20388, and pICH20999 containing the secretory signal peptides of rice alpha-amylase (GENBANK® accession no. P27932; SEQ ID NO: 18), *N. plumbagenifolia* calreticulin (GENBANK® accession no. Z71395; SEQ ID NO: 20), apple pectinase (GENBANK® accession no. P48978; SEQ ID NO: 22), barley alpha-amylase (GENBANK® accession no. CAX51374; SEQ ID NO: 24), respectively were used.

Once the vectors were assembled, plant expression of the cholera toxin B subunit variants was then performed using the magnICON® system. For expression of the cholera toxin B subunit variant polypeptide with the *V. cholerae* secretory signal (SEQ ID NO: 16), the three component plasmids, pNM47, pICH20111, and pICH14011, were used. For the cholera toxin B subunit variant polypeptides with the other secretory signals, the appropriate 5' provector (see above) was used in combination with pNM134 and pICH14011. The vectors were delivered via *Agrobacterium tumefaciens* into *N. benthamiana* leaves using vacuum infiltration methods. Briefly, midlogarithmic cultures of *A. tumefaciens* GV3101 harboring the plasmids were harvested, and bacteria were resuspended to $OD_{600}$ of 0.03 in 10 mM 2-(N-morpholino)ethanesulfonic acid (MES) buffer containing 10 mM $MgSO_4$, pH 5.5. The suspension was vacuum infiltrated into *N. benthamiana* leaves by using a vacuum pump.

After 4-7 days, leaf proteins were subsequently analyzed for cholera toxin B subunit variant polypeptide expression. Leaf material was homogenized by a Waring blender in extraction buffer (20 mM Tris-Cl, pH 5.0, 500 mM NaCl, 20 mM Ascorbic Acid, 10 mM Sodium Metabisulfate) and the extracts were filtered through four layers of cheese cloth followed by a single layer of Miracloth. The extracts were then heated at 50° C. for 25 minutes to precipitate plant endogenous proteins and starch and centrifuged at 22,100×g at 4° C. for 15 minutes followed by filtration through a 0.22 μm filter. The clarified extracts were then analyzed for cholera toxin B subunit variant polypeptide expression by SDS-PAGE and GM1-ganglioside-capture enzyme-linked immunosorbent assay (GM1-ELISA), as described previously [3,4] (FIGS. 1A-1B, respectively). Briefly, to perform the SDS-PAGE analysis, an aliquot of 5 μL of 4× Loading Dye (40% v/v glycerol, 8% w/v SDS. 4% v/v (3-mercaptoethanol, 0.08% w/v bromophenol blue) was added to 20 μL of the clarified leaf extracts and heated at 95° C. for 10 minutes. Samples were resolved using Lonza 15% Tris Glycine gels (Catalog No. 58510) in Bio-Rad gel boxes with 1×SDS running buffer (25 mM Tris, 192 mM glycine, 0.1% SDS, pH 8.3), and the gels were subsequently stained with Commassie Blue stain for 20 minutes at room temperature and then destained overnight at room temperature in Commassie destaining solution.

To perform the GM1-ELISA experiments, plates were coated with 50 μL/well of 2 μg/mL monosialoganglioside-GM1 (Sigma-Aldrich #G-7641) in coating buffer (15 mM $Na_2CO_3$, 35 mM $NaHCO_3$, pH 9.6) by incubating at 37° C. for 1 hour. Plates were blocked with 150 μL per well of 5% PBSTM (Phosphate Buffered Saline, pH 7.4, 0.05% [v/v] Tween 20, 5% Non-fat dry milk) for 1 hour at room temperature. Fifty μL per well of the clarified leaf extracts or a CTB standard (100 ng/mL to 1.56 ng/ml; Sigma-Aldrich, #C9903), serially diluted 2-fold in 1% PBSTM, were incubated for 1 hour at 37° C. The plate-bound CTB was detected by a goat anti-CTB antiserum (List Biological Laboratories #703) diluted at 1:5,000 in 1% PBSTM with a rabbit anti-goat IgG peroxidase-conjugated secondary antibody (Sigma, Catalog No. A5420) diluted 1:10,000 in 1% PBSTM and a chemiluminescence substrate (TMB Super Sensitive HRP Substrate, BioFX Laboratories # TMBS-1000-01). Plates were incubated with the primary and secondary antibodies for 1 hour at 37° C. The reaction was stopped with stop solution (0.6 N $H_2SO_4$, 1N HCl). Absorbance values at 450 nm were read on a Beckman Coulter DTX880 Multimode Detector. A standard curve was also generated, which was used to estimate the cholera toxin B subunit variant polypeptide concentrations in the clarified extracts.

Figure 1B:
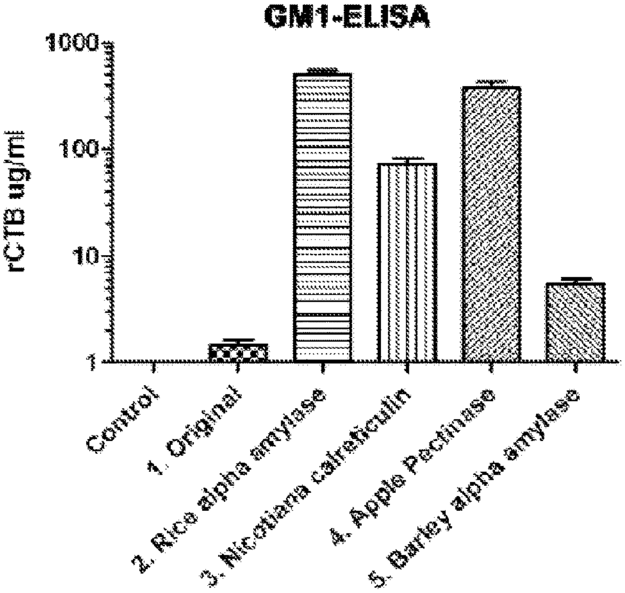

To accomplish the foregoing experiments, a non-viral vector was initially constructed for the stable expression of the cholera toxin B subunit variant polypeptides in transgenic plants, where the secretory signal used in the construct was the native secretory signal derived from *V. cholerae*. In spite of the attachment of the ER retention signal at the C-terminus of that cholera toxin B subunit variant polypeptide (SEQ ID NOS: 15 and 16), however, the cholera toxin B subunit variant polypeptide expression level was relatively low in those experiments, with only approximately 0.5 mg of the protein being obtained per kg of leaf material (FIG. 1A, Tg lane), as determined by GM1-ELISA. As such, to investigate whether transient expression based on a viral vector could provide higher expression of the same cholera toxin B subunit variant polypeptide (SEQ ID NOS: 15 and 16), the magnICON® vector was used due to its alleged ability to produce high-level protein expression in *N. benthamiana* [5]. However, the magnICON® vector also exhibited a low level of cholera toxin B subunit polypeptide expression, i.e., 0.2 mg/kg (FIG. 1A, lane 1; FIG. 1B, Original). In this regard, and without wishing to be bound by any particular theory, it was next hypothesized that the native *V. cholerae*-derived secretory signal may not function well in a plant cell, and that changing the signal could lead to an increase in cholera toxin B subunit variant polypeptide accumulation. As such, the *V. cholerae* secretory signal (corresponding to amino acids 1 to 21 of GENBANK® Accession no. AY475128) was replaced with the various other secretory signals of plant origin mentioned herein above and the additional cholera toxin B subunit variant polypeptides were analyzed using SDS-PAGE, these additional cholera toxin B subunit variant polypeptides included cholera toxin B subunit variant polypeptides having the secretory signal peptides of rice α-amylase (SEQ ID NO: 26, lane 2), *N. plumbagenifolia* calreticulin (SEQ ID NO: 27, lane 3), apple pectinase (SEQ ID NO: 28, lane 4), and barley α-amylase (SEQ ID NO: 29, lane 5). GM1-ELISA was also employed to screen different cholera toxin B subunit variant polypeptides having the various secretory signals for polypeptide expression in leaf extracts (FIG. 1B). Upon analysis of the results from these experiments, it was found that a secretory signal derived from rice α-amylase (SEQ ID NO: 18) provided the highest expression of cholera toxin B subunit variant polypeptides at levels up to 3 g/kg. Therefore, to perform the vaccine and immunological studies described further below, a cholera toxin B subunit variant polypeptide containing the rice α-amylase and the SEKDEL signal (SEQ ID NOS: 26) was produced.

One unique feature of the plant-produced cholera toxin B subunit variant polypeptides is the presence of an Asn (N)-linked glycan (NLG) at position 4 (SEQ ID NO: 6). The SDS-PAGE analysis shown in FIG. 1A, however, revealed that the glycosylation was not a uniform event, and, in particular, revealed that there was a heterogeneous population with 1 or 0 glycan per cholera toxin B subunit, represented by a band at around 14.5 kDa and 12.5 kDa, respectively. To eliminate the NLG and produce an aglycosylated cholera toxin B subunit variant polypeptides (SEQ ID NO: 4), site-directed mutagenesis was then preformed to mutate the AAC codon (Asn4) to AGC (Ser) as it was though that such a mutation would not affect CTB's structure or function (see, e.g., the *E. coli* heat-liable enterotoxin B subunit having a Ser amino acid at a corresponding position; GENBANK® Accession No. AAC60441).

Example 2

Expression of Aglycosylated Cholera Toxin B Subunit Variant in *Nicotiana benthamiana*

To characterize the aglycosylated cholera toxin B subunit variant polypeptide (SEQ ID NO: 4), an SDS-PAGE analysis of the Asn4→Ser cholera toxin B subunit variant expressed in *N. benthamiana* was conducted at 0, 4, 5, 6 and 7 days post magnICON® vector inoculation (dpi). Briefly, an aliquot of 10 μL of 2× native sample buffer (Bio-Rad No. 161-0738) was added to 20 μL of clarified leaf extracts. Samples were resolved using Lonza 15% Tris Glycine gels (Catalog No. 58510) in Bio-Rad gel boxes with 1× SDS running buffer (25 mM Tris, 192 mM glycine, 0.1% SDS, pH 8.3). The gels were stained with Commassie Blue stain for 20 minutes at room temperature and destained overnight at room temperature in Commassie destaining solution.

Figure 2:
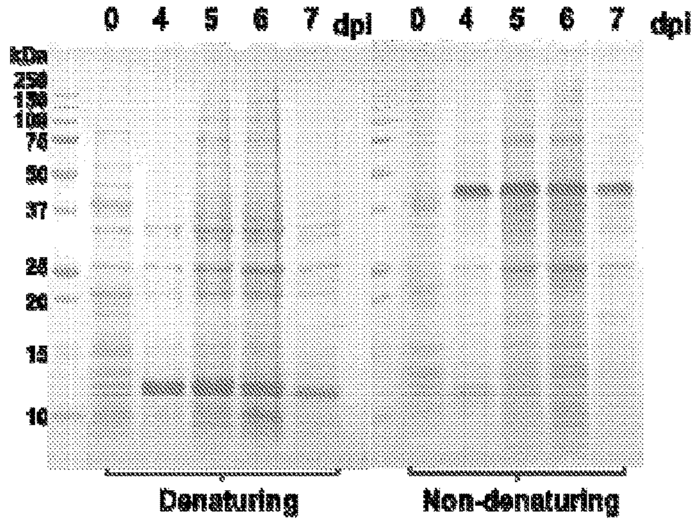
FIG. 2 is an image of a gel used for SDS-PAGE analysis of the expression of an aglycosylated cholera toxin B subunit variant polypeptide in *N. benthamiana;*

Upon analyzing the SDS-PAGE results, it was found that the Asn4→Ser mutation successfully eliminated the N-glycosylation, as shown by a single band at around 12 kDa under denaturing conditions, while retaining a pentameric form that is necessary for GM1-ganglioside binding activity, as shown by the single band at around 60 kDa on a non-reducing SDS-PAGE gel (FIG. 2). The expression of the aglycosylated cholera toxin B subunit variant polypeptide appeared to peak at 5 dpi, after which plants became very necrotic and expression levels began to decrease. GM1-ELISA showed that the aglycosylated cholera toxin B subunit variant polypeptide was expressed at 0.5-1.5 g/kg of leaf material, which was among the highest for the plant-based recombinant protein expression [5], even though it was not as high as its N-glycosylated counterpart.

Example 3

Purification of Cholera Toxin B Subunit Variants

Figure 3:
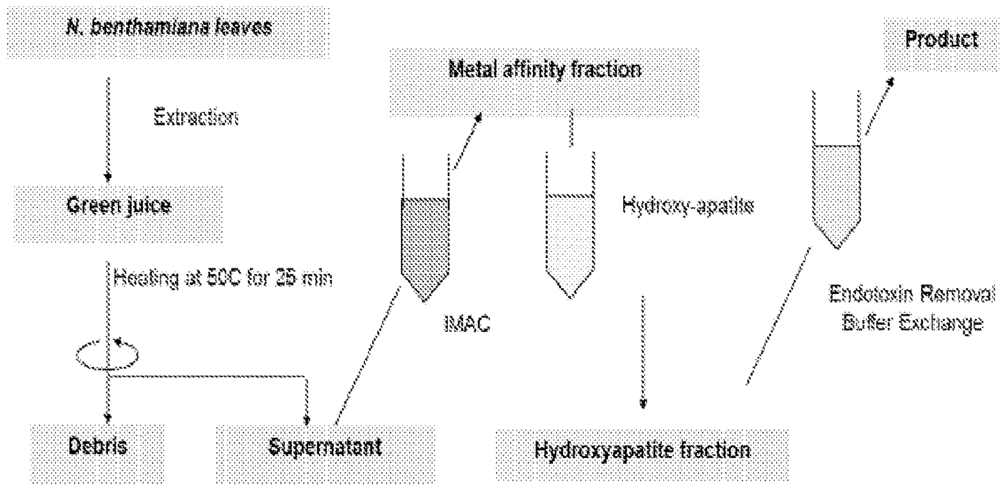
FIG. 3 is a schematic diagram showing an exemplary method for isolating a cholera toxin B subunit variant polypeptide from plant tissue in accordance with the presently-disclosed subject matter.

To purify the various cholera toxin B subunit variants produced by the foregoing methods, an immobilized metal affinity chromatography (IMAC) procedure was used as depicted in FIG. 3. Briefly, clarified leaf extracts were adjusted to pH 8 with a Tris, pH 9.0 buffer followed by filtration with a 0.22 μm filter. Chromatography was performed using an AKTA Purifier (GE Healthcare). Talon Superflow Metal Affinity Resin (Clontech No. 635670), packed in an XK-26 column (GE Healthcare), was equilibrated with 10 column volume (CV) of Talon equilibration buffer (20 mM Tris-Cl, pH 8.0, 500 mM NaCl). Samples were loaded at 2.5 ml/min. The column was washed with 8 CV of Talon equilibration buffer. The cholera toxin B subunit variant polypeptides were eluted with a step gradient using 100% Talon elution buffer (20 mM Tris-Cl, pH 8.0, 500 mM NaCl, 150 mM Imidazole) and collected by monitoring absorbance at 280 nm. SDS-PAGE was employed to verify the collected fraction for the presence of the cholera toxin B subunit variant polypeptides. The variant polypeptide fraction was further purified using a Bio-Rad CHT Hydroxyapatite Fast Flow 5 mL pre-packed column (Catalog No. 732-4324). The column was equilibrated with 10 CV of CHT equilibration buffer (10 mM Tris-Cl, pH 8.0, 5 mM sodium phosphate). The sample was loaded at a flow rate of 2.5 ml/min followed by a 10 CV wash with CHT equilibration buffer. The proteins were eluted using a gradient from 0 to 100% CHT elution buffer (10 mM Tris-Cl, pH 8.0, 500 mM sodium phosphate) over 20 CV. Five mL fractions were collected. The cholera toxin B subunit variant polypeptide-containing fractions, after verified by SDS-PAGE, were combined and endotoxin was removed using a Triton X-114 phase separation method. [5] After endotoxin removal, the cholera toxin B subunit variant polypeptides were ultrafiltrated and diafiltrated into sterile Dulbecco's PBS (Gibco No. 14190) using Amicon Ultra-15 3000 MWCO centrifugal devices (Millipore No. UFC900324) according to the manufacturer's instructions. Endotoxin levels were checked with a Charles River PTS Endotoxin test system, using 10-0.1 EU/mL cartridges (Charles River No. PTS201). Purity was determined to be greater than 95% via overloaded SDS-PAGE and size-exclusion HPLC.

In certain of the purification procedures, the purification procedure described above was shortened by eliminating the second CHT chromatography step and endotoxin removal, as it was found that the cholera toxin B subunit variant polypeptide purity was greater than 98% after the first Talon affinity step.

Example 4

Figure 4A:
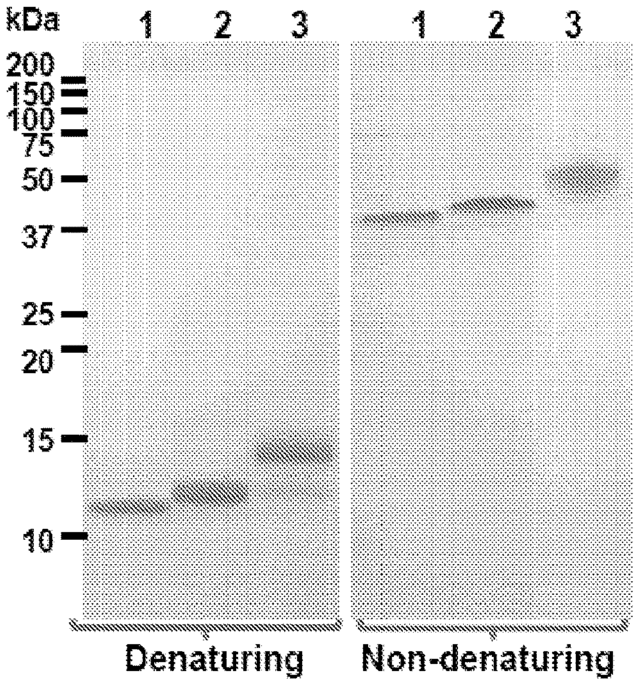
FIGS. 4A-4B are an image and a graph showing the results of a SDS-PAGE analysis of a wild-type (native) cholera toxin B subunit polypeptide, a plant-produced aglycosylated cholera toxin B subunit variant polypeptide, and a plant-produced N-glycosylated cholera toxin B subunit variant polypeptide, including an image of a denaturing and non-denaturing gel used for the SDS-PAGE analysis (FIG. 4A), and a graph showing the ability of the polypeptides to bind to GM1 ganglioside (FIG. 4B)

Comparison of Production of Native, Aglycosylated-Plant and N-Glycosylated-Plant Cholera Toxin B Subunit Variants To further evaluate the cholera toxin B subunit variant polypeptides produced above, experiments were performed to assess whether the *Nicotiana*-produced cholera toxin B subunit variant polypeptides were comparable to their native bacterial counterparts. Briefly, to perform these experiments, native cholera toxin B subunit polypeptides were first produced in *E. coli* as described previously [3], and the SDS-PAGE analysis was conducted using the *E. coli*-produced cholera toxin B subunit polypeptide and certain of the plant-made cholera toxin B subunit variant polypeptides produced above. As shown in FIG. 4A, the denaturing SDS-PAGE (left) showed each polypeptide in a monomeric form, with the native (lane 1) and the plant-made aglycosylated cholera toxin B subunit variant polypeptides (lane 2) both having a single band, whereas the plant-made N-glycosylated cholera toxin B subunit variant polypeptides (lane 3) showed two bands corresponding to approximately 78% N-glycosylated and 22% aglycosylated forms (based on a densitometric analysis). The non-denaturing SDS-PAGE (FIG. 4A, right) showed that native, plant-made aglycosylated, and plant-made N-glycosylated cholera toxin B subunits all retained pentamer formation. For both denaturing and non-denaturing SDS-PAGE analysis, 2 μg of purified proteins were loaded on the gels.

To then test whether the *Nicotiana*-produced N-glycosylated and aglycosylated cholera toxin B subunit variant polypeptides retained affinity for GM1-ganglioside, a competitive GM1-ELISA was performed. Briefly, to perform the competitive GM1 ELISA, a 96-well plate was coated and blocked as described above. In 1.5 mL tubes, serial dilutions of each cholera toxin B subunit variant polypeptides sample (SEQ ID NOS: 4 and 26) were then prepared in 1% PBSTM (1000, 500, 250, 125, 62.5, 31.3, 15.6, 7.8, 3.9, 2.0, 0.2 and 0 nM). To each cholera toxin B subunit variant polypeptide at each concentration, an equal volume of 2 μg/mL HRP-CTB (Molecular Probes #C34780) was then added and mixed. Then, 100 μL/well of each mixture (triplicates for each dilution) was added to the plate and incubated for 1 hour at 37° C. The plate-bound HRP-CTB was detected by adding a chemiluminescence substrate (TMB Super Sensitive HRP Substrate, BioFX Laboratories # TMBS-1000-01). The reaction was then stopped with stop solution (0.6 N $H_2SO_4$, 1 N HCl) and absorbance values at 450 nm were read on a Beckman Coulter DTX880 Multimode Detector. Fifty percent inhibitory concentrations (IC50) were determined by the GraphPad Prism 5.0 software.

Figure 4B:
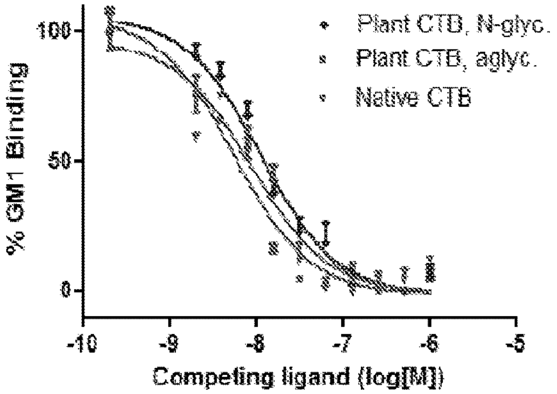

As shown in FIG. 4B, it was observed that there was no significant difference between their apparent affinities to the receptor; the native, plant-made aglycosylated and plant-made N-glycosylated cholera toxin B subunits each showed 50% inhibitory concentrations (IC50) of 8.97 nM, 5.65 nM, and 11.52 nM, respectively. The result demonstrated that the modifications made on plant-produced cholera toxin B subunit variant polypeptides, i.e., glycosylation, Asn4→Ser mutation, change of the secretory signal, and attachment of a C-terminal ER retention signal, did not affect the molecular binding properties of the cholera toxin B subunits.

Example 5

Antibody Responses to Cholera Toxin B Subunit Variants

Figure 5:
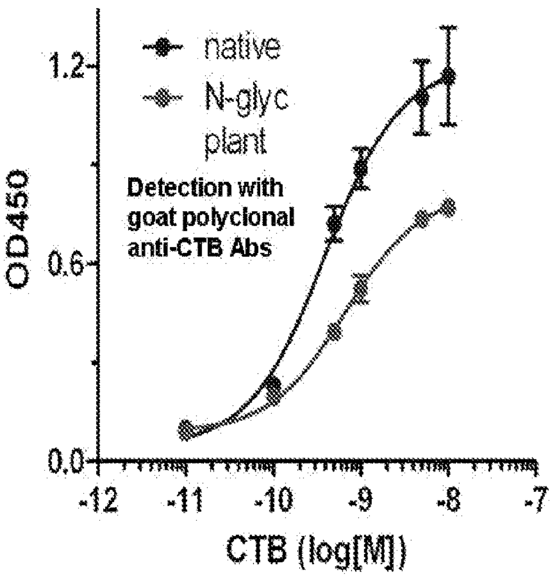
FIG. 5 is a graph showing the ability of a goat polyclonal anti-cholera toxin B antibody to bind to a plant-produced N-glycosylated cholera toxin B subunit variant polypeptide (N-glyc-plant) and to a wild-type cholera toxin B subunit polypeptide produced in *E. coli* (native)

To evaluate antibody responses to the cholera toxin B subunit variants of the presently-disclosed subject matter, a further GM1-ELISA was conducted using the procedures described above, where the concentration of native cholera toxin B subunits and plant-made, N-glycosylated cholera toxin B subunit variant polypeptides was determined using theoretical extinction coefficients at 280 nm of 0.8181 $(mg/mL)^{-1}$ $cm^{-1}$ and 0.7660 $(mg/mL)^{-1}$ $cm^{-1}$, respectively. As shown in FIG. 5, this additional GM1-ELISA showed that the goat polyclonal anti-CTB antisera bound less to plant-derived N-glycosylated cholera toxin B subunit variant polypeptide (SEQ ID NO: 6) than native cholera toxin B subunit produced in *E. coli* (as indicated by the arrow on the graph). The result indicated that the NLG prevented the access of some anti-CTB antibodies to their epitopes. Based on these results, it was thus believed that immunization with N-glycosylated cholera toxin B subunit variant polypeptide can direct an antibody response toward the more accessible GM1-binding site, which would in turn provide better neutralization of cholera toxin, i.e., higher vaccine efficacy against cholera.

Example 6

Biochemical Characterization of Native, Aglycosylated-Plant, and N-Glycosylated-Plant Cholera Toxin B Subunit Variants To further evaluate the native cholera toxin B subunit (SEQ ID NO: 2), plant-made aglycosylated cholera toxin B subunit variant polypeptides (SEQ ID NO: 4), and plant-made N-glycosylated cholera toxin B subunit variant polypeptides (SEQ ID NO: 6), biochemical characterizations of the polypeptides were conducted using size-exclusion chromatography-high performance liquid chromatography (SEC-HPLC) and a thermal shift assay. Briefly, the chromatography was performed on a Beckman Coulter System Gold HPLC. An aliquot of 17 μL, of the native, plant-made aglycosylated, and plant-made N-glycosylated cholera toxin B subunits at 1 mg/ml were applied, at 1.0 mL/min, to an SEC column (YMC-Pack Diol-200, 500×8.0 mm I.D., S-5 μm, 20 nm) equilibrated with 100 mM sodium phosphate, pH 7.0, 200 mM NaCl. After injection, 100 mM sodium phosphate, pH 7.0, 200 mM NaCl was applied to the column at flow rate of 1.0 mL/min for 35 minutes. Before and after polypeptide analysis, an aliquot of 17 μL, of gel filtration standards (Bio-Rad No. 151-1901) were applied to the column to confirm integrity of the SEC results. The gel filtration standards are a mixture of five proteins with molecular sizes of 660 kDa, 140 kDa, 45 kDa, 18 kDa, and 1.3 kDa. Polypeptide elution was monitored by absorbance at 280 nm.

For the thermal shift assay, the melting temperature of cholera toxin B subunit polypeptides were determined by using a fluorescence-based thermal shift assay performed on a Bio-Rad iQ5 multicolor real-time PCR system. Each polypeptide, at a final concentration of 60.0 μM in PBS, was mixed with a final concentration of 50× Sypro orange (Molecular Probes No. 5-6650) in a total volume of 20 μL in a 96 well plate (USA Scientific No. 1402-9200). Blank controls were set up for protein alone, and samples and blanks were analyzed in triplicate. The plate was set to be heated from 20° C. to 95° C. in 0.2° C. increments at interval of 15 seconds. Data were then plotted using the GraphPad Prism 5 software.

Figure 6A:
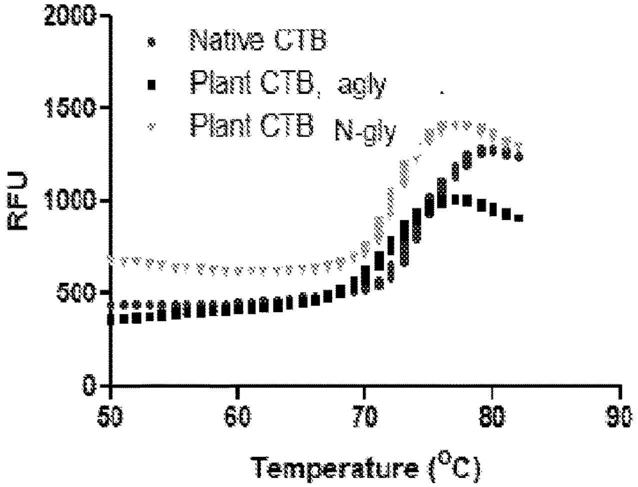
FIGS. 6A and 6B are graphs showing a comparison of a biochemical characterization of a wild-type (native) cholera toxin B subunit polypeptide, a plant-produced aglycosylated cholera toxin B subunit variant polypeptide (Plant CTB, agly), and a plant-produced N-glycosylated cholera toxin B subunit variant polypeptide (Plant CTB, N-gly), including a graph showing the results of a thermal shift assay used to determine the melting points of the three polypeptides (FIG. 6A) and a graph showing the results of a size exclusion chromatography-high performance liquid chromatography experiment used to determine the purity of the three polypeptides as produced (FIG. 6B)

The biochemical characterizations of the native cholera toxin B subunit polypeptide, plant-made aglycosylated cholera toxin B subunit variant polypeptides, and plant-made N-glycosylated cholera toxin B subunit variant polypeptides demonstrated that all of the polypeptides have similar purity and thermal stabilities. As shown in FIG. 6A, the fluorescence-based thermal shift assay, which was utilized to determine the melting temperatures of the polypeptide variants, revealed that the native cholera toxin B subunit polypeptides, plant-made aglycosylated cholera toxin B subunit variant polypeptides, and plant-made N-glycosylated cholera toxin B subunit variant polypeptides had melting temperatures of 75° C., 72.2° C., and 72.0° C., respectively, indicating that the modifications introduced into the sequence to generate the plant-made polypeptide variants did not compromise the thermal stability of the proteins.

Figure 6B:
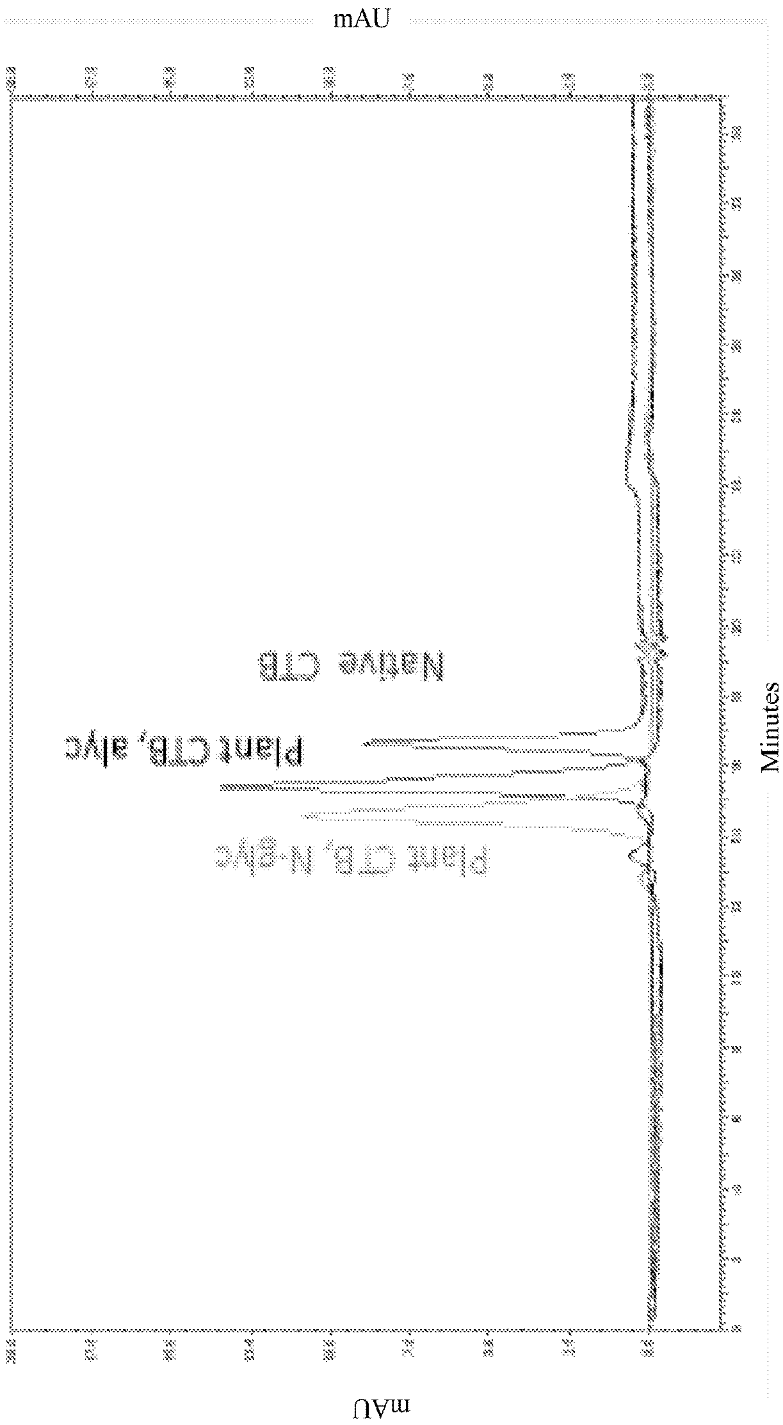

As shown in FIG. 6B, the SEC-HPLC was used to determine the purity of the polypeptides, and revealed that all of the polypeptides showed one large peak with greater than 95% of the peak area and a small peak at a shorter retention time. The elution time of the large peak roughly corresponded to the size of a pentamer form (50-60 kDa), such that the purity of the pentameric form was estimated to be greater than 95% for all of the polypeptides.

Example 7

Figure 7A:
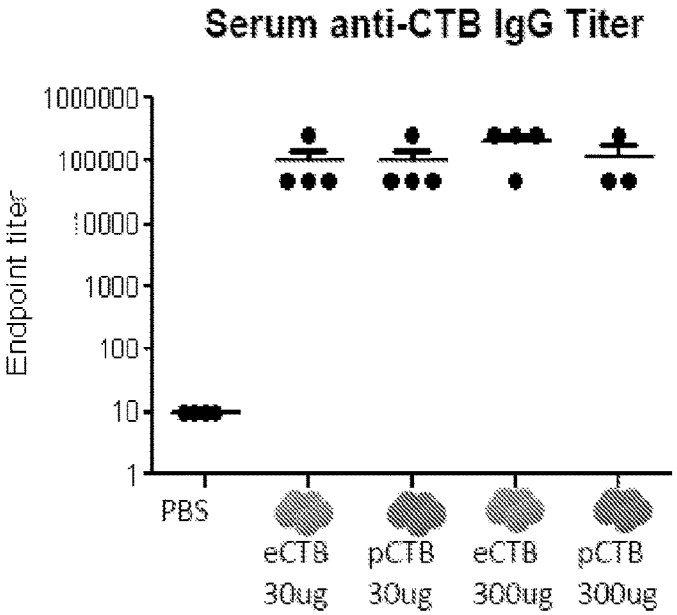
FIGS. 7A-7B are graphs showing the oral immunogenicity of a wild-type cholera toxin B subunit polypeptide produced in *E. coli* (eCTB) and a plant-produced aglycosylated cholera toxin B subunit variant polypeptide (pCTB), including a graph showing the endpoint titers of serum anti-cholera toxin B subunit IgG titer (FIG. 7A), and a graph showing the endpoint titers of intestinal anti-cholera toxin B subunit IgA titer (FIG. 7B)
Figure 7B:
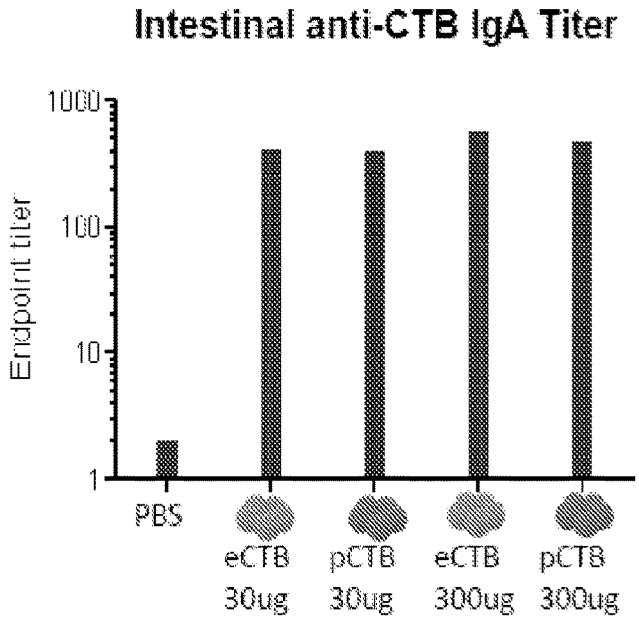
Figure 8:
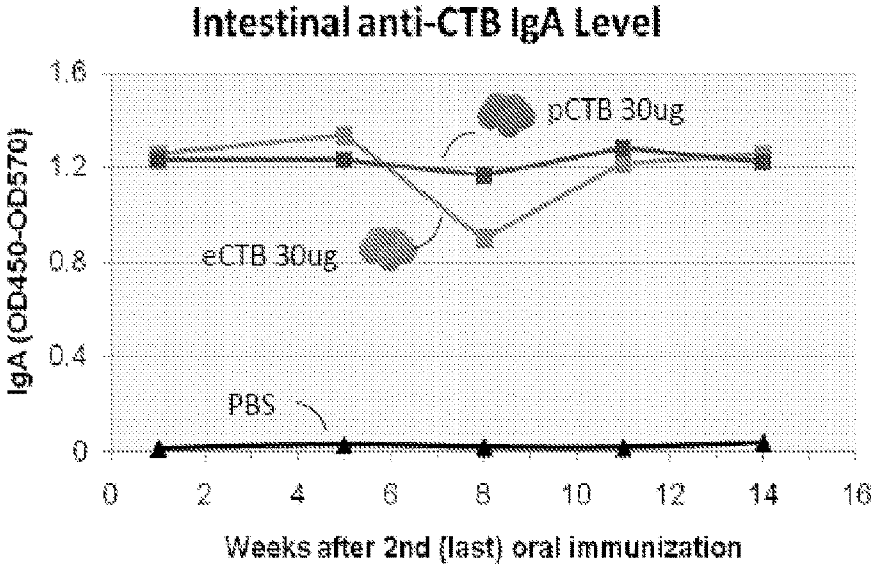
FIG. 8 is a graph showing the duration of intestinal anti-cholera toxin B subunit IgA titers in mice orally immunized with either a vehicle control (PBS), a wild-type cholera toxin B subunit polypeptide produced in *E. coli* (eCTB), or a plant-produced aglycosylated cholera toxin B subunit variant polypeptide (pCTB)

Oral Immunization with Bacterial-Produced Cholera Toxin B Subunit Variants and with Plant-Made Cholera Toxin B Subunit Variants To further assess the cholera toxin B subunit variant polypeptides of the presently-disclosed subject matter, an oral immunization experiment was performed in a mouse model to determine if there was a difference in an antibody response between the native (SEQ ID NO: 2) and plant-made aglycosylated polypeptides (SEQ ID NO: 4). C57bl/6 mice (four mice per group) were immunized twice by gavage with 30 or 300 μg of native cholera toxin B subunit polypeptide (produced in *E. coli*, referred to as "eCTB") or plant-made aglycosylated cholera toxin B subunit variant polypeptide ("pCTB") at Week 0 and 2. A control group was immunized with PBS vehicle. One week after the second immunization, serum and fecal pellets were collected, the endpoint titers of serum anti-CTB immunoglobulin (Ig)G and intestinal anti-CTB IgA were determined by ELISA, as described previously. [3,6]. Endpoint titers were defined as the reciprocal of sample dilutions giving a positive OD value after subtracting background in ELISA. As shown in FIGS. 7A and 7B, both eCTB and pCTB induced equivalent levels of serum anti-CTB IgG and intestinal anti-CTB IgA that was sustained for greater than 3.5 months (FIG. 8), indicating that the plant-produced aglycosylated cholera toxin B subunit polypeptide variants are immunologically equivalent to their native counterparts, and further indicating that the plant-produced aglycosylated variants can serve as a viable alternative to their bacterially-produced counterparts that are currently used in the oral cholera vaccine Dukoral.

Example 8

Cholera Toxin B Subunit Variants Having Increased N-Glycosylation

As described above, the initially produced cholera toxin B subunit variant polypeptides were N-glycosylated when expressed in plant cells, with one NLG being attached to Asn4 of the amino acid sequence to thereby comprise up to 5 NLGs per cholera toxin molecule given that cholera toxin B subunit is a homo-pentameric protein. Due to the C-terminal ER retention signal on the plant-expressed cholera toxin B subunits, the CTB-attached NLGs consist mainly of oligomannose sugars that are commonly known as H-Man glycans. [7] H-Man glycans are often abundantly displayed on the envelope glycoproteins of many enveloped viruses such as HIV, hepatitis C, Ebola, and influenza viruses. [8] However, it has been observed that such glycans are rare on host glycoproteins, particular in humans, as the human immune system makes use of mechanisms to sense and capture mannose-rich substances via the mannose-binding lectin (MBL) and C-type lectin receptors (CLR) on antigen presenting cells, such as the mannose receptor and Dendritic Cell-Specific Intercellular adhesion molecule-3-Grabbing Non-integrin (DC-SIGN). In this regard, it was thought that the "mannosylation" of immunogens may be one strategy to enhance the efficacy of vaccines, and it was hypothesized that N-glycosylated cholera toxin B subunit variant polypeptides could potentially be: (1) developed as a vaccine that would induce H-Man glycan-specific antibodies (Abs) exhibiting broad antiviral activity against enveloped viruses; and (2) developed as a vaccine scaffold to carry various antigens and efficiently stimulate mucosal and systemic immune systems. Additionally, from the results shown in FIG. 5 and as described above, it was believed that the N-glycosylated cholera toxin B subunit variant polypeptides would exhibit higher vaccine efficacy against cholera.

To assess the ability of N-glycosylated cholera toxin B subunit variant polypeptides to efficiently induce H-Man glycan-specific Abs and/or to assess whether the cholera toxin B subunit variant polypeptides can effectively be recognized by the immune system via CLR, experiments were undertaken to attempt to increase the number of NLGs on plant-produced cholera toxin B subunit variant polypeptides. In eukaryotic cells including plants, N-glycosylation of a newly synthesized polypeptide requires a tripeptide sequence composed of Asn-X-Ser/Thr ("sequon"; X is any amino acid but Pro) in its primary structure. In this regard, the amino acid sequence of the cholera toxin B subunit variant polypeptides was modified by means of site directed mutagenesis to have more than one sequon, besides the existing one at Asn4, and, more specifically, cholera toxin B subunit variant polypeptides were designed that had two and three sequons. For a two-sequon variant, the C-terminal extension peptide containing the ER retention signal was modified to Val-Thr-Lys-Asp-Glu-Leu (originally Ser-Glu-Lys-Asp-Glu-Leu) to create a sequon at Asn103-Val-Thr (SEQ ID NOS: 8 and 10). For a three-sequon variant, Lys23 was mutated to Thr to create a new sequon at Asn21-Asp22-Thr23 (SEQ ID NOS: 12 and 14). Without wishing to be bound by any particular theory, it was believed that the attachment of NLGs to those particular locations would not interfere with GM1 receptor-binding of CTB.

Once the additional cholera toxin B subunit variant polypeptides were designed and expressed using the magnICON® system described above, SDS-PAGE and lectin blot analysis using concanavalin A (ConA) were then performed to prove that CTB-VTKDEL (i.e., the construct containing 2 glycosylation sites) was successfully N-glycosylated upon expression in *Nicotiana benthamiana*. To perform these further analyses, the SDS-PAGE analysis was performed as described above. The lectin blot was performed by first using an SDS-PAGE gel to resolve mono- and di-N-glycosylated cholera toxin B subunit variant polypeptides under denaturing conditions, as described above. The cholera toxin B subunit variant polypeptides were then transferred to a PVDF membrane (Millipore No. IPSN07852) for 1 hour at 100 volts. The membrane was subsequently blocked by PBS containing 2% (v/v) TWEEN 20 for 2 minutes at room temperature and incubated with 2 μg/mL of ConA-HRP (Sigma No. L6397) in BS containing 0.05% (v/v) TWEEN 20 with 1 mM $CaCl_2$, 1 mM $MnCl_2$, 1 mM $MgCl_2$ for 16 hours at room temperature. The membrane-bound ConA was then detected using the Amersham ECL Western Blotting Analysis System (GE Healthcare No. RPN2108) according to the manufacturer's instructions.

Figure 9:
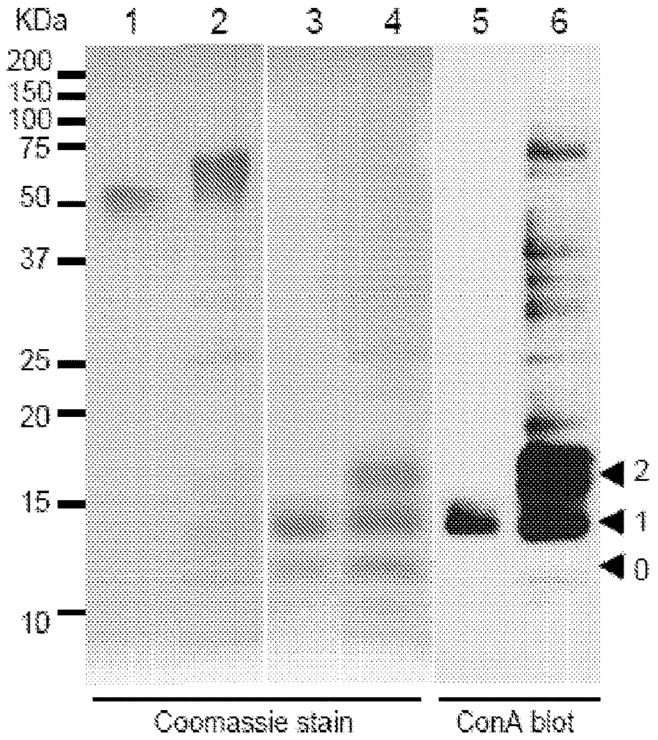
FIG. 9 is an image of gels showing an SDS-PAGE and lectin blot analysis of a mono-N-glycosylated cholera toxin B subunit variant polypeptide (lanes 1, 3, and 5) and a di-N-glycosylated cholera toxin B subunit variant polypeptide (lanes 2, 4, and 6) including an image of Coomassie stained gels under non-denaturing (lanes 1 and 2) and denaturing (lanes 3 and 4) conditions, and an image of a concanavalin A blot used to detect the glycosylated polypeptides (lanes 5 and 6)

Upon analysis of the results from this experiment, it was observed that both mono- and di-N-glycosylated cholera toxin B subunit variant polypeptides retained pentamer formation as shown by a band at approximately 60 kDa on the non-denaturing SDS-PAGE (FIG. 9, Lanes 1 and 2, respectively). The denaturing SDS-PAGE further demonstrated that the mono-N-glycosylated cholera toxin B subunit variant polypeptides had two different forms of the monomer subunit, with 1 and 0 NLG (FIG. 9, Lane 3). Densitometry analysis showed that the ratio of 1 and 0 NLG forms was 7.8:2.2. The di-N-glycosylated cholera toxin B subunit variant polypeptides had three different forms of the monomer subunit with 2, 1, and 0 NLGs (FIG. 9, Lane 3). Densitometry analysis revealed that the ratio of 2, 1, and 0 N-glycosylated forms was 3.9:4.3:1.7. The lectin blot using ConA, a lectin having high affinity for Man residues of NLGs, showed that both 1- and 2-NLGs-attached cholera toxin B subunit variant polypeptides were recognized by ConA (FIG. 9, Lanes 5 and 6), indicating that both the mono- and di-N-glycosylated cholera toxin B subunit variant polypeptides contained Man residues.

Figure 10:
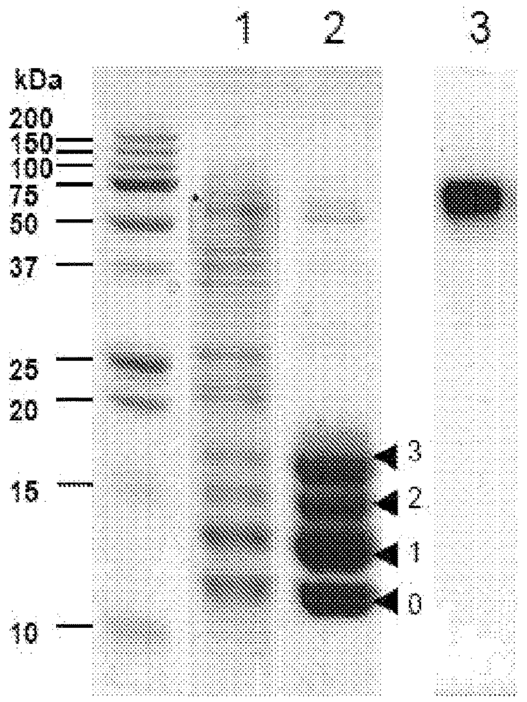
FIG. 10 is an image of gels showing an SDS-PAGE analysis of a tri-N-glycosylated cholera toxin B subunit variant polypeptide, including an image of a Coomassie-stained gel under denaturing conditions (crude extract, lane 1; purified product, lane 2) and an image of a Coomassie-stained gel under non-denaturing conditions (purified product, lane 3)

Similar experiments were also performed with the *Nicotiana*-produced [$Thr^{23}$]-CTB-VTKDEL (tri-N-glycosylated cholera toxin B subunit variant polypeptide). The denaturing SDS-PAGE (FIG. 10, Lanes 1 and 2) showed that four different forms (with 3, 2, 1, and 0 NLGs) of the monomer subunits were expressed, providing evidence that the Lys23→Thr mutation resulted in a successful addition of a third NLG. As shown by the non-denaturing SDS-PAGE (FIG. 10, Lane 3), tri-N-glycosylated cholera toxin B subunit variant polypeptides were purified to greater than 98% purity and retained pentamer formation (band at 60-70 kDa). Furthermore, GM1-ELISA has confirmed that tri-N-glycosylated cholera toxin B subunit variant polypeptides bind to GM1-ganglioside.

Example 9

Analysis of N-Glycosylation of Cholera Toxin B Subunit Variants

To further analyze the N-glycosylation of the cholera toxin B subunit variant polypeptides of the presently-disclosed subject matter, Peptide: N-Glycosidase F (PNGase F), an amidase that cleaves between the innermost N-acetylglucosamine and Asn residues of H-Man, hybrid, and complex NLGs (except for those with α-1,3-linked core fucose found in plants) from glycoproteins was used along with endoglycosidase H (Endo H), a glycosidase that cleaves within the chitobiose core of H-Man Glycans and some hybrid oligosaccharides from N-glycosylated glycoproteins. [7] Briefly, the N-glycosylated cholera toxin B subunit variant polypeptides (SEQ ID NO: 26) were first expressed in *N. benthamiana* grown with and without the chemical inhibitor of class 1 α mannosidases, kifunensine. For expression of mono-N-glycosylated cholera toxin B subunit variant polypeptides with kifunensine, the plants were vector-inoculated as outlined above, except that roots were removed from the soil and placed in water containing 580 ng/ml kifunensine (Cayman Chemical Company No. 10009437) after vector inoculation. The plants were re-treated with freshly prepared kifunensine at 2 and 4 dpi and harvested at 5 dpi.

For Endo H Digestion, Endo H and buffers were purchased from New England BioLabs (Catalog No. P0703S), and two μg of cholera toxin B subunit variant polypeptides, 1 μL of 10× Glycoprotein Denaturing Buffer and $H_2O$ were mixed to make a 10 μl total reaction volume. N-glycosylated cholera toxin B subunit variant polypeptide was denatured by heating at 100° C. for 10 minutes. The total reaction volume was adjusted to 20 μL by adding 2 μL of 10× G5 Reaction Buffer, 4 μL of Endo H and $H_2O$. The reaction was performed at 37° C. overnight.

For PNGase F Digestion, PNGase F and buffers were purchased from New England BioLabs (Catalog No. P0704S). Two μg of cholera toxin B subunit variant polypeptides, 1 μL of 10× Glycoprotein Denaturing Buffer and $H_2O$ were mixed to make a 10 μL total reaction volume. N-glycosylated cholera toxin B subunit variant polypeptide was denatured by heating at 100° C. for 10 minutes. The total reaction volume was adjusted to 20 μL by adding 2 μL 10× G7 Reaction Buffer, 2 μL 10% NP40, 2 μL PNGase F and $H_2O$. The reaction was performed at 37° C. overnight.

Figure 11:
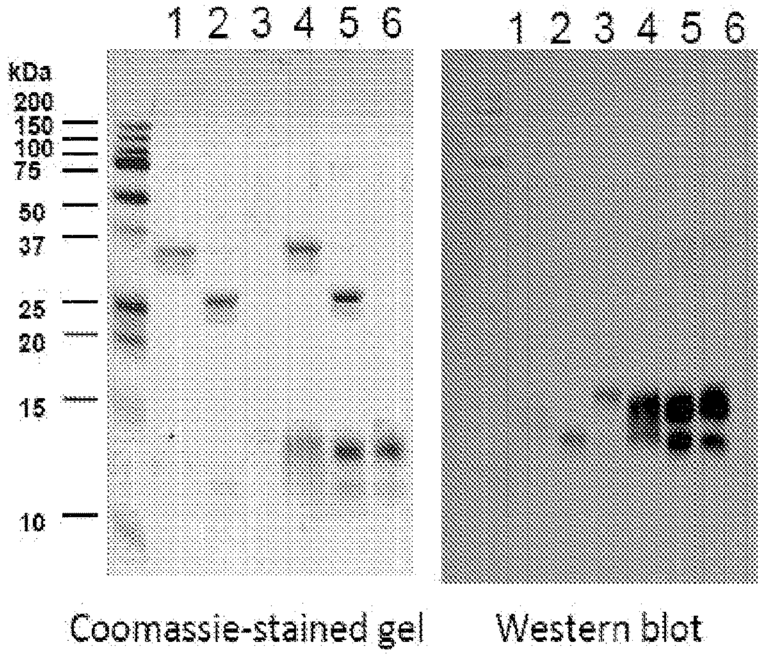
FIG. 11 includes images of a gel used for SDS-PAGE analysis and Western blot analysis of Endoglycosidase H (Endo H) and Peptide: N-Glycosidase F (PNGase F) digestion of a mono-N-glycoslyated cholera toxin B subunit variant polypeptide obtained from *N. benthamiana* and grown with and without a chemical inhibitor (CI) of class I α-mannosidases, including an analysis of mono-N-glycosylated cholera toxin B subunit variant polypeptide (+CI) digested with PNGase F (lanes 1), mono-N-glycosylated cholera toxin B subunit variant polypeptide (+CI) digested with Endo H (lanes 2), undigested mono-N-glycosylated cholera toxin B subunit variant polypeptide (+CI) (lanes 3), mono-N-glycosylated cholera toxin B subunit variant polypeptide digested with PNGase F (lanes 4), mono-glycosylated cholera toxin B subunit variant polypeptide digested with Endo H (lanes 5), and undigested mono-N-glycosylated cholera toxin B subunit variant polypeptide (lanes 6)

After digestions, SDS-PAGE and western blot analysis, using a goat anti-CTB antiserum as described above, showed that mono-N-glycosylated cholera toxin B subunit variant polypeptides produced in *N. benthamiana* was only partially cleaved by PNGase F and Endo H (FIG. 11, Lanes 4-6), indicating that NLGs attached to the cholera toxin B subunit variant polypeptides were not uniform and contain fewer H-Man glycans than expected. To obtain more uniform H-Man glycan-displaying cholera toxin B subunit variant polypeptides, mono-N-glycosylated cholera toxin B subunit variant polypeptides were expressed in *N. benthamiana* treated with kifunensine. SDS-PAGE and western blot showed that NLGs of mono-N-glycosylated cholera toxin B subunit variant polypeptides produced in the presence of the kifunensine were completely cleaved by PNGase F and Endo H, which indicated that NLGs attached to cholera toxin B subunit variant polypeptides can be restricted to uniform HMGs by inhibiting the α-mannosidases of the host.

Example 10

Recognition of Cholera Toxin B Subunit Variants by DC-SIGN Receptor

To evaluate whether the cholera toxin B subunit variants of the presently-disclosed subject matter were capable of being recognized the DC-SIGN receptor, the mono- and tri-N-glycosylated cholera toxin B subunit variant polypeptides produced above were tested for DC-SIGN binding using ELISA. Briefly, a 96-well plate was coated with monosialoganglioside-GM1 as described above. Plates were then blocked with 150 μL per well with 5% BSA in TCN buffer (10 mM Tris, 50 mM $CaCl_2$, 150 mM NaCl pH 7.4), overnight at 4° C. Fifty μL/well of 2-fold serially diluted cholera toxin B subunit variant polypeptides samples (starting from 10 μg/mL) in 1% BSA in TCN were incubated for 1 hour at 37° C. Next, 50 μL/well of recombinant DC-SIGN (rhDC-SIGN/Fc chimera, R&D Systems No. 161-DC) diluted at 0.5 μg/mL in 1% BSA in TCN was added and incubated for 2 hours at room temperature. Bound DC-SIGN was detected by mouse anti-human IgG (Fc-specific)-HRP conjugate (diluted at 1:10,000 in 1% BSA in TCN; Southern Biotech No. 9040-05) and chemiluminescence (TMB Super Sensitive HRP Substrate, BioFX Laboratories No. TMBS-1000-01). The reaction was stopped with stop solution ($0.6NH_2SO_4$, 1N HCL) and absorbance values at 450 nm were read on a Beckman Coulter DTX880 Multimode Detector. Data were analyzed using GraphPad Prism 5.

Figure 12:
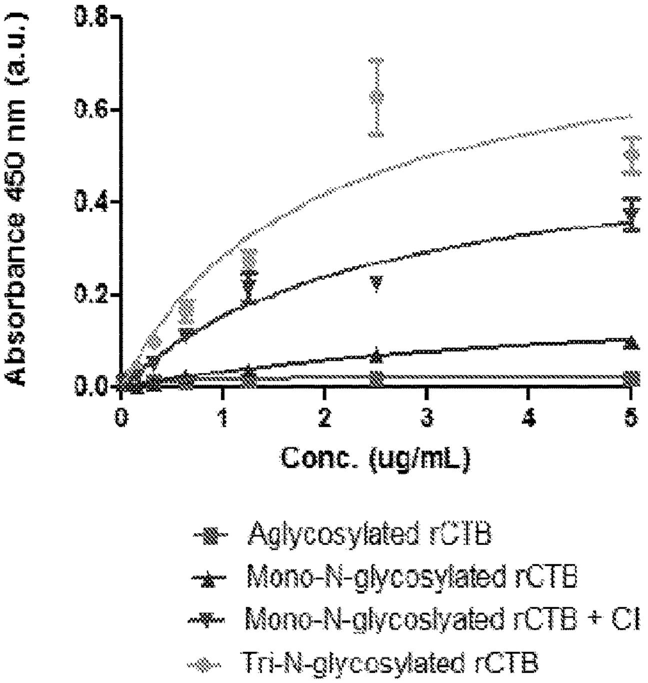
FIG. 12 is a graph showing the extent of recognition of an aglycosylated cholera toxin B subunit variant polypeptide, a mono-N-glycosylated cholera toxin B subunit variant polypeptide, a mono-N-glycosylated cholera toxin B subunit variant polypeptide grown in a plant exposed to a chemical inhibitor (CI) of class I α mannosidases, and a tri-N-glycosylated cholera toxin B subunit variant polypeptide, where the recognition is occurring by the pattern recognition C-type lectin receptor DC-SIGN (Dendritic Cell-Specific Intercellular adhesion molecule-3-Grabbing Non-integrin)

Upon analysis of the results from this experiment, it was found that the N-glycosylated cholera toxin B subunit variant polypeptides, but not the aglycosylated counterpart, were recognized by DC-SIGN. The CLR bound tri-N-glycosylated cholera toxin B subunit variant polypeptides better than the mono-N-glycosylated protein, indicating that additional NLGs attached to cholera toxin B subunit variant polypeptides enhanced DC-SIGN recognition. This in turn indicated that N-glycosylated cholera toxin B subunit variant polypeptides can be used as a scaffold to target antigens to DCs. Furthermore, as shown in FIG. 12, it was found that mono-N-glycosylated cholera toxin B subunit variant polypeptides (SEQ ID NO: 6) produced in kifunensine-treated plants (i.e., displaying only H-Man glycans) was significantly more captured by DC-SIGN than the protein produced under the normal conditions.

Example 11

Figure 13:
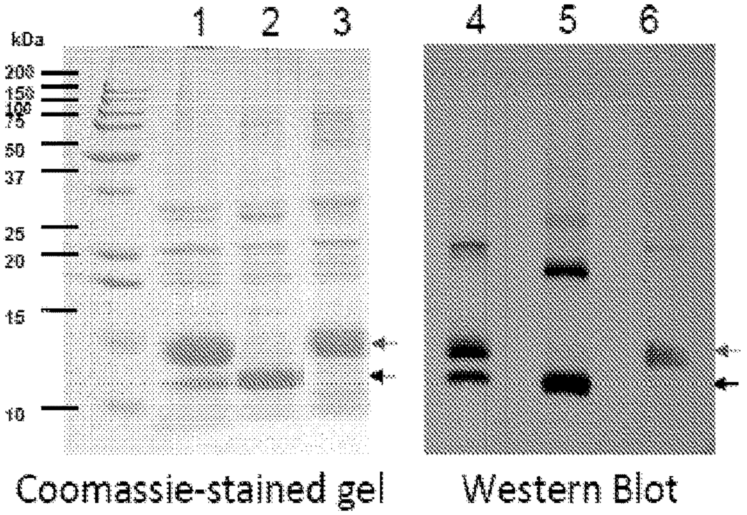
FIG. 13 includes images of gels showing SDS-PAGE and Western blot analysis of two mutations (S26C and A102C) introduced into a mono-N-glycosylated cholera toxin B subunit variant polypeptide, including images of a Coomassie-stained gel (lanes 1-3) and a Western blot (lanes 4-6) under denaturing conditions, where a mono-N-glycosylated cholera toxin B subunit variant polypeptide was loaded onto lanes 1 and 4, an aglycosylated cholera toxin B subunit variant polypeptide was loaded onto lanes 2 and 5, and a mono-glycosylated cholera toxin B subunit variant polypeptide with the S26C and A102C mutations was loaded onto lanes 3 and 6.

Mutagenesis of Cholera Toxin B Subunit Variants for Binding of Homogenous Population N-Linked Glycans As described above and shown in FIG. 13 (Lanes 1 and 4), *Nicotiana*-produced mono-N-glycosylated cholera toxin B subunit variant polypeptides displayed a heterogeneous population of NLGs with 1 and 0 glycan per monomer. In conducting these experiments, however, it was also found that Ser26→Cys and Ala102→Cys mutations of the cholera toxin B subunit (SEQ ID NO: 25), which were produced via site-directed mutagenesis and were originally intended for inter-subunit disulfide bond formation, resulted in a homogeneous population of N-glycosylated cholera toxin B subunit monomer with one NLG (FIG. 13, Lanes 3 and 6) that is desirable for the use of N-glycosylated cholera toxin B subunit variant polypeptides.

Throughout this document, various references are mentioned, including publications, patents, and patent applications. All such references, including the references set forth in the following list, are incorporated herein by reference to the same extent as if each individual publication, patent, or patent application was specifically and individually indicated to be incorporated by reference.

REFERENCES

1. Marillonnet S, Giritch A, Gils M, Kandzia R, Klimyuk V, Gleba Y. In planta engineering of viral RNA replicons: efficient assembly by recombination of DNA modules delivered by *Agrobacterium*. Proc Natl Acad Sci USA. 2004; 101(18): 6852-7.
2. Gleba Y, Klimyuk V, Marillonnet S. Magnifection—a new platform for expressing recombinant vaccines in plants. Vaccine. 2005; 23(17-18): 2042-8.
3. Matoba N, Magerus A, Geyer B C, Zhang Y, Muralidharan M, Alfsen A, et al. A mucosally targeted subunit vaccine candidate eliciting HIV-1 transcytosis-blocking Abs. Proc Natl Acad Sci USA. 2004; 101(37): 13584-9.
4. Matoba N, Griffin T A, Mittman M, Doran J D, Hanson C V, Montefiori D, et al. Transcytosis-blocking Abs elicited by an oligomeric immunogen based on the membrane proximal region of HIV-1 gp41 target non-neutralizing epitopes. Curr HIV Res. 2008; 6(3): 218-29.
5. Matoba N, Davis K R, Palmer K E. Recombinant Protein Expression in *Nicotiana*. Methods Mol. Biol. 2011; 701: 199-219.
6. Matoba N, Geyer B C, Kilbourne J, Alfsen A, Bomsel M, Mor T S. Humoral immune responses by prime-boost heterologous route immunizations with CTB-MPR(649-684), a mucosal subunit HIV/AIDS vaccine candidate. Vaccine. 2006; 24(23): 5047-55.
7. Matoba N, Kajiura H, Chemi I, Doran J D, Bomsel M, Fujiyama K, et al. Biochemical and immunological characterization of the plant-derived candidate human immunodeficiency virus type 1 mucosal vaccine CTB-MPR (649-684). Plant Biotechnol J. 2009; 7(2): 129-45.
8. Balzarini J. Targeting the glycans of glycoproteins: a novel paradigm for antiviral therapy. Nat Rev Microbiol. 2007; 5(8): 583-97.
9. Irache J M, Salman H H, Gamazo C, Espuelas S. Mannose-targeted systems for the delivery of therapeutics. Expert Opin Drug Deliv. 2008; 5(6): 703-24.
10. Keler T, Ramakrishna V, Fanger M W. Mannose receptor-targeted vaccines. Expert opinion on biological therapy. 2004; 4(12): 1953-62.
11. Sheng K C, Kalkanidis M, Pouniotis D S, Esparon S, Tang C K, Apostolopoulos V, et al. Delivery of antigen using a novel mannosylated dendrimer potentiates immunogenicity in vitro and in vivo. Eur J. Immunol. 2008; 38(2): 424-36.

It will be understood that various details of the presently disclosed subject matter can be changed without departing from the scope of the subject matter disclosed herein. Furthermore, the foregoing description is for the purpose of illustration only, and not for the purpose of limitation.

What is claimed is:

1. An isolated polypeptide produced in a plant cell, the isolated polypeptide comprising the sequence of SEQ ID NO: 4.

2. The polypeptide of claim 1, wherein the polypeptide further comprises a secretory signal peptide selected from the group consisting of a rice alpha-amylase secretory signal peptide, a *Nicotiana plumbagenifolia* calreticulin secretory signal peptide, an apple pectinase secretory signal peptide, and a barley alpha-amylase secretory signal peptide.

3. The polypeptide of claim 2, wherein the secretory signal peptide has an amino acid sequence selected from the group consisting of SEQ ID NOS: 18, 20, 22,and 24.

4. The polypeptide of claim 2, wherein the secretory signal peptide comprises the rice alpha-amylase secretory signal peptide.

5. A pharmaceutical composition comprising the polypeptide of claim 1 and a pharmaceutically-acceptable vehicle, carrier, or excipient.

6. The pharmaceutical composition of claim 5, wherein the pharmaceutical composition further comprises an adjuvant.

* * * * *

SEQUENCE LISTING

```
<160> NUMBER OF SEQ ID NOS: 31

<210> SEQ ID NO 1
<211> LENGTH: 309
<212> TYPE: DNA
<213> ORGANISM: Vibrio cholerae
```

<400> SEQUENCE: 1
accccacaaa acatcactga cttgtgtgct gagtaccaca acacccaaat ccacaccctc 60
aatgacaaga tctttagcta caccgagagc cttgctggca agagggagat ggctatcatc 120
accttcaaga atggtgctac cttccaagtg gaggtgcctg gaagccaaca cattgatagc 180
caaaagaagg ccattgagag gatgaaggac acacttagga tagcttacct cactgaggct 240
aaggtggaga agctttgtgt gtggaacaac aagacccccc atgctattgc tgccatcagc 300
atggccaac 309

<210> SEQ ID NO 2
<211> LENGTH: 103
<212> TYPE: PRT
<213> ORGANISM: Vibrio cholerae

<400> SEQUENCE: 2

Thr Pro Gln Asn Ile Thr Asp Leu Cys Ala Glu Tyr His Asn Thr Gln
1               5                   10                  15

Ile His Thr Leu Asn Asp Lys Ile Phe Ser Tyr Thr Glu Ser Leu Ala
            20                  25                  30

Gly Lys Arg Glu Met Ala Ile Ile Thr Phe Lys Asn Gly Ala Thr Phe
        35                  40                  45

Gln Val Glu Val Pro Gly Ser Gln His Ile Asp Ser Gln Lys Lys Ala
    50                  55                  60

Ile Glu Arg Met Lys Asp Thr Leu Arg Ile Ala Tyr Leu Thr Glu Ala
65                  70                  75                  80

Lys Val Glu Lys Leu Cys Val Trp Asn Asn Lys Thr Pro His Ala Ile
                85                  90                  95

Ala Ala Ile Ser Met Ala Asn
            100

<210> SEQ ID NO 3
<211> LENGTH: 327
<212> TYPE: DNA
<213> ORGANISM: Artificial Sequence
<220> FEATURE:
<223> OTHER INFORMATION: Cholera Toxin B Subunit Polypeptide Variant
      Polypeptide

<400> SEQUENCE: 3
accccacaaa gcatcactga cttgtgtgct gagtaccaca acacccaaat ccacaccctc 60
aatgacaaga tctttagcta caccgagagc cttgctggca agagggagat ggctatcatc 120
accttcaaga atggtgctac cttccaagtg gaggtgcctg gaagccaaca cattgatagc 180
caaaagaagg ccattgagag gatgaaggac acacttagga tagcttacct cactgaggct 240
aaggtggaga agctttgtgt gtggaacaac aagacccccc atgctattgc tgccatcagc 300
atggccaact ccgagaagga tgaactc 327

<210> SEQ ID NO 4
<211> LENGTH: 109
<212> TYPE: PRT
<213> ORGANISM: Artificial Sequence
<220> FEATURE:
<223> OTHER INFORMATION: Cholera Toxin B Subunit Polypeptide Variant
      Polypeptide

<400> SEQUENCE: 4

Thr Pro Gln Ser Ile Thr Asp Leu Cys Ala Glu Tyr His Asn Thr Gln

-continued

```
1               5                   10                  15

Ile His Thr Leu Asn Asp Lys Ile Phe Ser Tyr Thr Glu Ser Leu Ala
            20                  25                  30

Gly Lys Arg Glu Met Ala Ile Ile Thr Phe Lys Asn Gly Ala Thr Phe
        35                  40                  45

Gln Val Glu Val Pro Gly Ser Gln His Ile Asp Ser Gln Lys Lys Ala
    50                  55                  60

Ile Glu Arg Met Lys Asp Thr Leu Arg Ile Ala Tyr Leu Thr Glu Ala
65                  70                  75                  80

Lys Val Glu Lys Leu Cys Val Trp Asn Asn Lys Thr Pro His Ala Ile
                85                  90                  95

Ala Ala Ile Ser Met Ala Asn Ser Glu Lys Asp Glu Leu
            100                 105


<210> SEQ ID NO 5
<211> LENGTH: 327
<212> TYPE: DNA
<213> ORGANISM: Artificial Sequence
<220> FEATURE:
<223> OTHER INFORMATION: Cholera Toxin B Subunit Polypeptide Variant
      Polypeptide

<400> SEQUENCE: 5

accccacaaa acatcactga cttgtgtgct gagtaccaca acacccaaat ccacaccctc      60

aatgacaaga tctttagcta caccgagagc cttgctggca agagggagat ggctatcatc     120

accttcaaga atggtgctac cttccaagtg gaggtgcctg gaagccaaca cattgatagc     180

caaaagaagg ccattgagag gatgaaggac acacttagga tagcttacct cactgaggct     240

aaggtggaga agctttgtgt gtggaacaac aagacccccc atgctattgc tgccatcagc     300

atggccaact ccgagaagga tgaactc                                         327


<210> SEQ ID NO 6
<211> LENGTH: 109
<212> TYPE: PRT
<213> ORGANISM: Artificial Sequence
<220> FEATURE:
<223> OTHER INFORMATION: Cholera Toxin B Subunit Polypeptide Variant
      Polypeptide

<400> SEQUENCE: 6

Thr Pro Gln Asn Ile Thr Asp Leu Cys Ala Glu Tyr His Asn Thr Gln
1               5                   10                  15

Ile His Thr Leu Asn Asp Lys Ile Phe Ser Tyr Thr Glu Ser Leu Ala
            20                  25                  30

Gly Lys Arg Glu Met Ala Ile Ile Thr Phe Lys Asn Gly Ala Thr Phe
        35                  40                  45

Gln Val Glu Val Pro Gly Ser Gln His Ile Asp Ser Gln Lys Lys Ala
    50                  55                  60

Ile Glu Arg Met Lys Asp Thr Leu Arg Ile Ala Tyr Leu Thr Glu Ala
65                  70                  75                  80

Lys Val Glu Lys Leu Cys Val Trp Asn Asn Lys Thr Pro His Ala Ile
                85                  90                  95

Ala Ala Ile Ser Met Ala Asn Ser Glu Lys Asp Glu Leu
            100                 105


<210> SEQ ID NO 7
<211> LENGTH: 327
<212> TYPE: DNA
```

<213> ORGANISM: Artificial Sequence
<220> FEATURE:
<223> OTHER INFORMATION: Cholera Toxin B Subunit Polypeptide Variant Polypeptide

<400> SEQUENCE: 7
accccacaaa acatcactga cttgtgtgct gagtaccaca acacccaaat ccacaccctc 60
aatgacaaga tctttagcta caccgagagc cttgctggca agagggagat ggctatcatc 120
accttcaaga atggtgctac cttccaagtg gaggtgcctg gaagccaaca cattgatagc 180
caaaagaagg ccattgagag gatgaaggac acacttagga tagcttacct cactgaggct 240
aaggtggaga agctttgtgt gtggaacaac aagaccccc atgctattgc tgccatcagc 300
atggccaacg ttactaagga tgaactc 327

<210> SEQ ID NO 8
<211> LENGTH: 109
<212> TYPE: PRT
<213> ORGANISM: Artificial Sequence
<220> FEATURE:
<223> OTHER INFORMATION: Cholera Toxin B Subunit Polypeptide Variant Polypeptide

<400> SEQUENCE: 8

Thr Pro Gln Asn Ile Thr Asp Leu Cys Ala Glu Tyr His Asn Thr Gln
1 5 10 15

Ile His Thr Leu Asn Asp Lys Ile Phe Ser Tyr Thr Glu Ser Leu Ala
20 25 30

Gly Lys Arg Glu Met Ala Ile Ile Thr Phe Lys Asn Gly Ala Thr Phe
35 40 45

Gln Val Glu Val Pro Gly Ser Gln His Ile Asp Ser Gln Lys Lys Ala
50 55 60

Ile Glu Arg Met Lys Asp Thr Leu Arg Ile Ala Tyr Leu Thr Glu Ala
65 70 75 80

Lys Val Glu Lys Leu Cys Val Trp Asn Asn Lys Thr Pro His Ala Ile
85 90 95

Ala Ala Ile Ser Met Ala Asn Val Thr Lys Asp Glu Leu
100 105

<210> SEQ ID NO 9
<211> LENGTH: 327
<212> TYPE: DNA
<213> ORGANISM: Artificial Sequence
<220> FEATURE:
<223> OTHER INFORMATION: Cholera Toxin B Subunit Polypeptide Variant Polypeptide

<400> SEQUENCE: 9
accccacaaa acatcactga cttgtgtgct gagtaccaca acacccaaat ccacaccctc 60
aatgacacta tctttagcta caccgagagc cttgctggca agagggagat ggctatcatc 120
accttcaaga atggtgctac cttccaagtg gaggtgcctg gaagccaaca cattgatagc 180
caaaagaagg ccattgagag gatgaaggac acacttagga tagcttacct cactgaggct 240
aaggtggaga agctttgtgt gtggaacaac aagaccccc atgctattgc tgccatcagc 300
atggccaact ccgagaagga tgaactc 327

<210> SEQ ID NO 10
<211> LENGTH: 109
<212> TYPE: PRT
<213> ORGANISM: Artificial Sequence
<220> FEATURE:
<223> OTHER INFORMATION: Cholera Toxin B Subunit Polypeptide Variant
Polypeptide

<400> SEQUENCE: 10

```
Thr Pro Gln Asn Ile Thr Asp Leu Cys Ala Glu Tyr His Asn Thr Gln
1               5                   10                  15

Ile His Thr Leu Asn Asp Thr Ile Phe Ser Tyr Thr Glu Ser Leu Ala
            20                  25                  30

Gly Lys Arg Glu Met Ala Ile Ile Thr Phe Lys Asn Gly Ala Thr Phe
        35                  40                  45

Gln Val Glu Val Pro Gly Ser Gln His Ile Asp Ser Gln Lys Lys Ala
    50                  55                  60

Ile Glu Arg Met Lys Asp Thr Leu Arg Ile Ala Tyr Leu Thr Glu Ala
65                  70                  75                  80

Lys Val Glu Lys Leu Cys Val Trp Asn Asn Lys Thr Pro His Ala Ile
                85                  90                  95

Ala Ala Ile Ser Met Ala Asn Ser Glu Lys Asp Glu Leu
            100                 105
```

<210> SEQ ID NO 11
<211> LENGTH: 327
<212> TYPE: DNA
<213> ORGANISM: Artificial Sequence
<220> FEATURE:
<223> OTHER INFORMATION: Cholera Toxin B Subunit Polypeptide Variant
Polypeptide

<400> SEQUENCE: 11

```
accccacaaa acatcactga cttgtgtgct gagtaccaca acacccaaat ccacaccctc      60

aatgacacta tctttagcta caccgagagc cttgctggca agagggagat ggctatcatc     120

accttcaaga atggtgctac cttccaagtg gaggtgcctg gaagccaaca cattgatagc     180

caaaagaagg ccattgagag gatgaaggac acacttagga tagcttacct cactgaggct     240

aaggtggaga agctttgtgt gtggaacaac aagaccccc atgctattgc tgccatcagc     300

atggccaacg ttactaagga tgaactc                                         327
```

<210> SEQ ID NO 12
<211> LENGTH: 109
<212> TYPE: PRT
<213> ORGANISM: Artificial Sequence
<220> FEATURE:
<223> OTHER INFORMATION: Cholera Toxin B Subunit Polypeptide Variant
Polypeptide

<400> SEQUENCE: 12

```
Thr Pro Gln Asn Ile Thr Asp Leu Cys Ala Glu Tyr His Asn Thr Gln
1               5                   10                  15

Ile His Thr Leu Asn Asp Thr Ile Phe Ser Tyr Thr Glu Ser Leu Ala
            20                  25                  30

Gly Lys Arg Glu Met Ala Ile Ile Thr Phe Lys Asn Gly Ala Thr Phe
        35                  40                  45

Gln Val Glu Val Pro Gly Ser Gln His Ile Asp Ser Gln Lys Lys Ala
    50                  55                  60

Ile Glu Arg Met Lys Asp Thr Leu Arg Ile Ala Tyr Leu Thr Glu Ala
65                  70                  75                  80

Lys Val Glu Lys Leu Cys Val Trp Asn Asn Lys Thr Pro His Ala Ile
                85                  90                  95
```

-continued

```
Ala Ala Ile Ser Met Ala Asn Val Thr Lys Asp Glu Leu
            100                 105
```

<210> SEQ ID NO 13
<211> LENGTH: 345
<212> TYPE: DNA
<213> ORGANISM: Artificial Sequence
<220> FEATURE:
<223> OTHER INFORMATION: Cholera Toxin B Subunit Polypeptide Variant Polypeptide

<400> SEQUENCE: 13

```
accccacaaa acatcactga cttgtgtgct gagtaccaca acacccaaat ccacaccctc     60

aatgacacta tctttagcta caccgagagc cttgctggca agagggagat ggctatcatc    120

accttcaaga atggtgctac cttccaagtg gaggtgcctg gaagccaaca cattgatagc    180

caaaagaagg ccattgagag gatgaaggac acacttagga tagcttacct cactgaggct    240

aaggtggaga agctttgtgt gtggaacaac aagacccccc atgctattgc tgccatcagc    300

atggccaacg ttactggtgg tggaggatcc gagaaggatg aactc                    345
```

<210> SEQ ID NO 14
<211> LENGTH: 115
<212> TYPE: PRT
<213> ORGANISM: Artificial Sequence
<220> FEATURE:
<223> OTHER INFORMATION: Cholera Toxin B Subunit Polypeptide Variant Polypeptide

<400> SEQUENCE: 14

```
Thr Pro Gln Asn Ile Thr Asp Leu Cys Ala Glu Tyr His Asn Thr Gln
1               5                   10                  15

Ile His Thr Leu Asn Asp Thr Ile Phe Ser Tyr Thr Glu Ser Leu Ala
            20                  25                  30

Gly Lys Arg Glu Met Ala Ile Ile Thr Phe Lys Asn Gly Ala Thr Phe
        35                  40                  45

Gln Val Glu Val Pro Gly Ser Gln His Ile Asp Ser Gln Lys Lys Ala
    50                  55                  60

Ile Glu Arg Met Lys Asp Thr Leu Arg Ile Ala Tyr Leu Thr Glu Ala
65                  70                  75                  80

Lys Val Glu Lys Leu Cys Val Trp Asn Asn Lys Thr Pro His Ala Ile
                85                  90                  95

Ala Ala Ile Ser Met Ala Asn Val Thr Gly Gly Gly Gly Ser Glu Lys
            100                 105                 110

Asp Glu Leu
        115
```

<210> SEQ ID NO 15
<211> LENGTH: 393
<212> TYPE: DNA
<213> ORGANISM: Artificial Sequence
<220> FEATURE:
<223> OTHER INFORMATION: Cholera Toxin B Subunit Polypeptide Variant Polypeptide

<400> SEQUENCE: 15

```
atggctatca agctcaagtt tggagtgttc ttcactgtgc tccttagctc tgcctatgca     60

catggcaccc cacaaaacat cactgacttg tgtgctgagt accacaacac ccaaatccac    120

accctcaatg acaagatctt tagctacacc gagagccttg ctggcaagag ggagatggct    180

atcatcacct tcaagaatgg tgctaccttc caagtggagg tgcctggaag ccaacacatt    240
```

gatagccaaa agaaggccat tgagaggatg aaggacacac ttaggatagc ttacctcact 300
gaggctaagg tggagaagct ttgtgtgtgg aacaacaaga ccccccatgc tattgctgcc 360
atcagcatgg ccaactccga gaaggatgaa ctc 393

<210> SEQ ID NO 16
<211> LENGTH: 131
<212> TYPE: PRT
<213> ORGANISM: Artificial Sequence
<220> FEATURE:
<223> OTHER INFORMATION: Cholera Toxin B Subunit Polypeptide Variant Polypeptide

<400> SEQUENCE: 16

```
Met Ala Ile Lys Leu Lys Phe Gly Val Phe Phe Thr Val Leu Leu Ser
1               5                   10                  15

Ser Ala Tyr Ala His Gly Thr Pro Gln Asn Ile Thr Asp Leu Cys Ala
            20                  25                  30

Glu Tyr His Asn Thr Gln Ile His Thr Leu Asn Asp Lys Ile Phe Ser
        35                  40                  45

Tyr Thr Glu Ser Leu Ala Gly Lys Arg Glu Met Ala Ile Ile Thr Phe
    50                  55                  60

Lys Asn Gly Ala Thr Phe Gln Val Glu Val Pro Gly Ser Gln His Ile
65                  70                  75                  80

Asp Ser Gln Lys Lys Ala Ile Glu Arg Met Lys Asp Thr Leu Arg Ile
                85                  90                  95

Ala Tyr Leu Thr Glu Ala Lys Val Glu Lys Leu Cys Val Trp Asn Asn
            100                 105                 110

Lys Thr Pro His Ala Ile Ala Ala Ile Ser Met Ala Asn Ser Glu Lys
        115                 120                 125

Asp Glu Leu
    130
```

<210> SEQ ID NO 17
<211> LENGTH: 78
<212> TYPE: DNA
<213> ORGANISM: Oryza sativa

<400> SEQUENCE: 17
atggggaagc aaatggccgc cctgtgtggc tttctcctcg tggcgttgct ctggctcacg 60
cccgacgtcg cgcatggt 78

<210> SEQ ID NO 18
<211> LENGTH: 26
<212> TYPE: PRT
<213> ORGANISM: Oryza sativa

<400> SEQUENCE: 18

```
Met Gly Lys Gln Met Ala Ala Leu Cys Gly Phe Leu Leu Val Ala Leu
1               5                   10                  15

Leu Trp Leu Thr Pro Asp Val Ala His Gly
            20                  25
```

<210> SEQ ID NO 19
<211> LENGTH: 81
<212> TYPE: DNA
<213> ORGANISM: Nicotiana plumbaginifolia

<400> SEQUENCE: 19
atggctactc aacgaagggc aaaccctagc tctctccatc taattactgt attctctctg 60
ctcgtcgctg tcgtctcagg t 81

<210> SEQ ID NO 20
<211> LENGTH: 27
<212> TYPE: PRT
<213> ORGANISM: Nicotiana plumbaginifolia

<400> SEQUENCE: 20

Met Ala Thr Gln Arg Arg Ala Asn Pro Ser Ser Leu His Leu Ile Thr
1 5 10 15

Val Phe Ser Leu Leu Val Ala Val Val Ser Gly
20 25

<210> SEQ ID NO 21
<211> LENGTH: 78
<212> TYPE: DNA
<213> ORGANISM: Malus domestica

<400> SEQUENCE: 21
atggcattga agacacagtt gttgtggtca ttcgtggttg tgttcgttgt gtccttcagt 60
acaacttcat gctcaggt 78

<210> SEQ ID NO 22
<211> LENGTH: 26
<212> TYPE: PRT
<213> ORGANISM: Malus domestica

<400> SEQUENCE: 22

Met Ala Leu Lys Thr Gln Leu Leu Trp Ser Phe Val Val Val Phe Val
1 5 10 15

Val Ser Phe Ser Thr Thr Ser Cys Ser Gly
20 25

<210> SEQ ID NO 23
<211> LENGTH: 72
<212> TYPE: DNA
<213> ORGANISM: Hordeum vulgare

<400> SEQUENCE: 23
atggcgaaca aacacttgtc cctctccctc ttcctcgtcc tccttggcct gtcggccagc 60
ttggcctcag gt 72

<210> SEQ ID NO 24
<211> LENGTH: 24
<212> TYPE: PRT
<213> ORGANISM: Hordeum vulgare

<400> SEQUENCE: 24

Met Ala Asn Lys His Leu Ser Leu Ser Leu Phe Leu Val Leu Leu Gly
1 5 10 15

Leu Ser Ala Ser Leu Ala Ser Gly
20

<210> SEQ ID NO 25
<211> LENGTH: 109
<212> TYPE: PRT
<213> ORGANISM: Artificial Sequence
<220> FEATURE:
<223> OTHER INFORMATION: Cholera Toxin B Subunit Polypeptide Variant
Polypeptide

<400> SEQUENCE: 25

Thr Pro Gln Asn Ile Thr Asp Leu Cys Ala Glu Tyr His Asn Thr Gln
1               5                   10                  15

Ile His Thr Leu Asn Asp Lys Ile Phe Cys Tyr Thr Glu Ser Leu Ala
            20                  25                  30

Gly Lys Arg Glu Met Ala Ile Ile Thr Phe Lys Asn Gly Ala Thr Phe
        35                  40                  45

Gln Val Glu Val Pro Gly Ser Gln His Ile Asp Ser Gln Lys Lys Ala
    50                  55                  60

Ile Glu Arg Met Lys Asp Thr Leu Arg Ile Ala Tyr Leu Thr Glu Ala
65                  70                  75                  80

Lys Val Glu Lys Leu Cys Val Trp Asn Asn Lys Thr Pro His Ala Ile
                85                  90                  95

Ala Ala Ile Ser Met Cys Asn Ser Glu Lys Asp Glu Leu
            100                 105

<210> SEQ ID NO 26
<211> LENGTH: 135
<212> TYPE: PRT
<213> ORGANISM: Artificial Sequence
<220> FEATURE:
<223> OTHER INFORMATION: Cholera Toxin B Subunit Polypeptide Variant
      Polypeptide

<400> SEQUENCE: 26

Met Gly Lys Gln Met Ala Ala Leu Cys Gly Phe Leu Leu Val Ala Leu
1               5                   10                  15

Leu Trp Leu Thr Pro Asp Val Ala His Gly Thr Pro Gln Asn Ile Thr
            20                  25                  30

Asp Leu Cys Ala Glu Tyr His Asn Thr Gln Ile His Thr Leu Asn Asp
        35                  40                  45

Lys Ile Phe Ser Tyr Thr Glu Ser Leu Ala Gly Lys Arg Glu Met Ala
    50                  55                  60

Ile Ile Thr Phe Lys Asn Gly Ala Thr Phe Gln Val Glu Val Pro Gly
65                  70                  75                  80

Ser Gln His Ile Asp Ser Gln Lys Lys Ala Ile Glu Arg Met Lys Asp
                85                  90                  95

Thr Leu Arg Ile Ala Tyr Leu Thr Glu Ala Lys Val Glu Lys Leu Cys
            100                 105                 110

Val Trp Asn Asn Lys Thr Pro His Ala Ile Ala Ala Ile Ser Met Ala
        115                 120                 125

Asn Ser Glu Lys Asp Glu Leu
    130                 135

<210> SEQ ID NO 27
<211> LENGTH: 136
<212> TYPE: PRT
<213> ORGANISM: Artificial Sequence
<220> FEATURE:
<223> OTHER INFORMATION: Cholera Toxin B Subunit Polypeptide Variant
      Polypeptide

<400> SEQUENCE: 27

Met Ala Thr Gln Arg Arg Ala Asn Pro Ser Ser Leu His Leu Ile Thr
1               5                   10                  15

Val Phe Ser Leu Leu Val Ala Val Val Ser Gly Thr Pro Gln Asn Ile
            20                  25                  30

Thr Asp Leu Cys Ala Glu Tyr His Asn Thr Gln Ile His Thr Leu Asn

```
        35                  40                  45

Asp Lys Ile Phe Ser Tyr Thr Glu Ser Leu Ala Gly Lys Arg Glu Met
    50                  55                  60

Ala Ile Ile Thr Phe Lys Asn Gly Ala Thr Phe Gln Val Glu Val Pro
65                  70                  75                  80

Gly Ser Gln His Ile Asp Ser Gln Lys Lys Ala Ile Glu Arg Met Lys
                85                  90                  95

Asp Thr Leu Arg Ile Ala Tyr Leu Thr Glu Ala Lys Val Glu Lys Leu
            100                 105                 110

Cys Val Trp Asn Asn Lys Thr Pro His Ala Ile Ala Ala Ile Ser Met
        115                 120                 125

Ala Asn Ser Glu Lys Asp Glu Leu
    130                 135


<210> SEQ ID NO 28
<211> LENGTH: 135
<212> TYPE: PRT
<213> ORGANISM: Artificial Sequence
<220> FEATURE:
<223> OTHER INFORMATION: Cholera Toxin B Subunit Polypeptide Variant
      Polypeptide

<400> SEQUENCE: 28

Met Ala Leu Lys Thr Gln Leu Leu Trp Ser Phe Val Val Val Phe Val
1               5                   10                  15

Val Ser Phe Ser Thr Thr Ser Cys Ser Gly Thr Pro Gln Asn Ile Thr
            20                  25                  30

Asp Leu Cys Ala Glu Tyr His Asn Thr Gln Ile His Thr Leu Asn Asp
        35                  40                  45

Lys Ile Phe Ser Tyr Thr Glu Ser Leu Ala Gly Lys Arg Glu Met Ala
    50                  55                  60

Ile Ile Thr Phe Lys Asn Gly Ala Thr Phe Gln Val Glu Val Pro Gly
65                  70                  75                  80

Ser Gln His Ile Asp Ser Gln Lys Lys Ala Ile Glu Arg Met Lys Asp
                85                  90                  95

Thr Leu Arg Ile Ala Tyr Leu Thr Glu Ala Lys Val Glu Lys Leu Cys
            100                 105                 110

Val Trp Asn Asn Lys Thr Pro His Ala Ile Ala Ala Ile Ser Met Ala
        115                 120                 125

Asn Ser Glu Lys Asp Glu Leu
    130                 135


<210> SEQ ID NO 29
<211> LENGTH: 133
<212> TYPE: PRT
<213> ORGANISM: Artificial Sequence
<220> FEATURE:
<223> OTHER INFORMATION: Cholera Toxin B Subunit Polypeptide Variant
      Polypeptide

<400> SEQUENCE: 29

Met Ala Asn Lys His Leu Ser Leu Ser Leu Phe Leu Val Leu Leu Gly
1               5                   10                  15

Leu Ser Ala Ser Leu Ala Ser Gly Thr Pro Gln Asn Ile Thr Asp Leu
            20                  25                  30

Cys Ala Glu Tyr His Asn Thr Gln Ile His Thr Leu Asn Asp Lys Ile
        35                  40                  45

Phe Ser Tyr Thr Glu Ser Leu Ala Gly Lys Arg Glu Met Ala Ile Ile
```

-continued

```
    50                  55                  60

Thr Phe Lys Asn Gly Ala Thr Phe Gln Val Glu Val Pro Gly Ser Gln
65                  70                  75                  80

His Ile Asp Ser Gln Lys Lys Ala Ile Glu Arg Met Lys Asp Thr Leu
                85                  90                  95

Arg Ile Ala Tyr Leu Thr Glu Ala Lys Val Glu Lys Leu Cys Val Trp
            100                 105                 110

Asn Asn Lys Thr Pro His Ala Ile Ala Ala Ile Ser Met Ala Asn Ser
        115                 120                 125

Glu Lys Asp Glu Leu
    130


<210> SEQ ID NO 30
<211> LENGTH: 6
<212> TYPE: PRT
<213> ORGANISM: Artificial Sequence
<220> FEATURE:
<223> OTHER INFORMATION: Endoplasmic Reticulum Retention Signal

<400> SEQUENCE: 30

Ser Glu Lys Asp Glu Leu
1               5


<210> SEQ ID NO 31
<211> LENGTH: 4
<212> TYPE: PRT
<213> ORGANISM: Artificial Sequence
<220> FEATURE:
<223> OTHER INFORMATION: Endoplasmic Reticulum Retention Signal

<400> SEQUENCE: 31

Lys Asp Glu Leu
1
```